United States Patent
Uehara

(10) Patent No.: US 9,706,962 B1
(45) Date of Patent: Jul. 18, 2017

(54) APPARATUS AND METHOD FOR TEACHING AND ALGORITHMS FOR IDENTIFYING QUALIFYING MOVEMENTS

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 69 days.

(21) Appl. No.: 14/789,136

(22) Filed: Jul. 1, 2015

Related U.S. Application Data

(63) Continuation-in-part of application No. 14/132,808, filed on Dec. 18, 2013, now Pat. No. 9,226,706.

(60) Provisional application No. 62/019,522, filed on Jul. 1, 2014, provisional application No. 61/739,160, filed on Dec. 19, 2012, provisional application No. 62/027,409, filed on Jul. 22, 2014.

(51) Int. Cl.
| | |
|---|---|
| *A61B 5/00* | (2006.01) |
| *A63B 24/00* | (2006.01) |
| *A61B 5/11* | (2006.01) |
| *A61B 5/22* | (2006.01) |

(52) U.S. Cl.
CPC .......... *A61B 5/7267* (2013.01); *A61B 5/0004* (2013.01); *A61B 5/1107* (2013.01); *A61B 5/1114* (2013.01); *A61B 5/1123* (2013.01); *A61B 5/224* (2013.01); *A61B 5/486* (2013.01); *A63B 24/0062* (2013.01)

(58) Field of Classification Search
CPC ........ A63B 24/0006; A63B 2024/0012; A63B 2024/0015; A63B 2024/0071; A63B 24/0062; A63B 24/0003; A61B 5/7267; A61B 5/72; A61B 5/0004; A61B 5/1107; A61B 5/1114; A61B 5/1123; A61B 5/224; A61B 5/486
USPC ....................................................... 73/379.01
See application file for complete search history.

(56) References Cited

U.S. PATENT DOCUMENTS

| | | | | |
|---|---|---|---|---|
| 6,185,451 B1* | 2/2001 | Richardson | .......... | A61B 5/0488 600/546 |
| 2002/0143277 A1* | 10/2002 | Wood | .................. | A61B 5/1071 600/595 |
| 2002/0170193 A1* | 11/2002 | Townsend | ............. | A61B 5/1116 33/512 |
| 2008/0001735 A1* | 1/2008 | Tran | .................... | G06F 19/3418 340/539.22 |
| 2009/0131759 A1* | 5/2009 | Sims | .................... | A61B 5/1135 600/301 |

(Continued)

*Primary Examiner* — Lisa Caputo
*Assistant Examiner* — Philip Cotey
(74) *Attorney, Agent, or Firm* — Staniford Tomita LLP

(57) ABSTRACT

A wearable device has user movement sensors and core contraction sensors. Signals from the sensors are transmitted to a processor which analyzes the movement signals and determines when a qualifying movement is performed which benefits from core contraction. Signals from the core contraction sensors are also transmitted to the processor and are used to determine if the core is contracted during the qualifying movement. If the core is contracted during the qualifying movement, the movement is a protected qualifying movement. However, if the core is not contracted during the qualifying movement the movement is an unprotected qualifying movement. The system can inform the user when unprotected qualifying movements are performed.

20 Claims, 19 Drawing Sheets

(56) References Cited

U.S. PATENT DOCUMENTS

2011/0269601 A1* 11/2011 Nelson ................... A47C 7/021
                                                            482/8
2012/0259648 A1* 10/2012 Mallon ............... G06F 19/3418
                                                            705/2

* cited by examiner

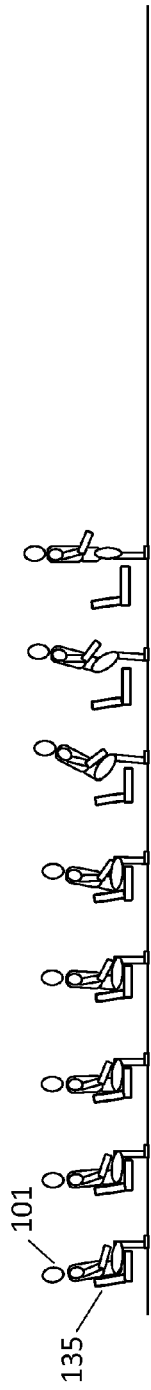
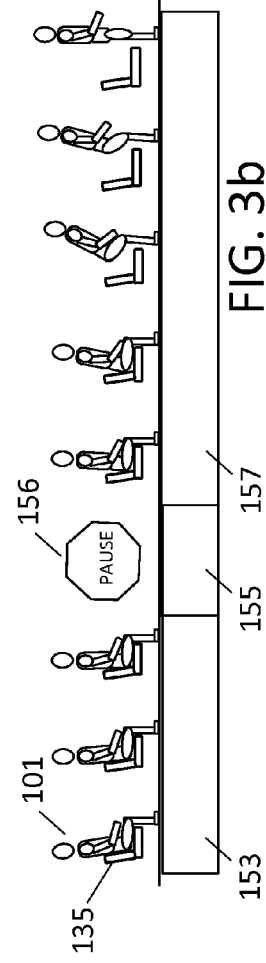
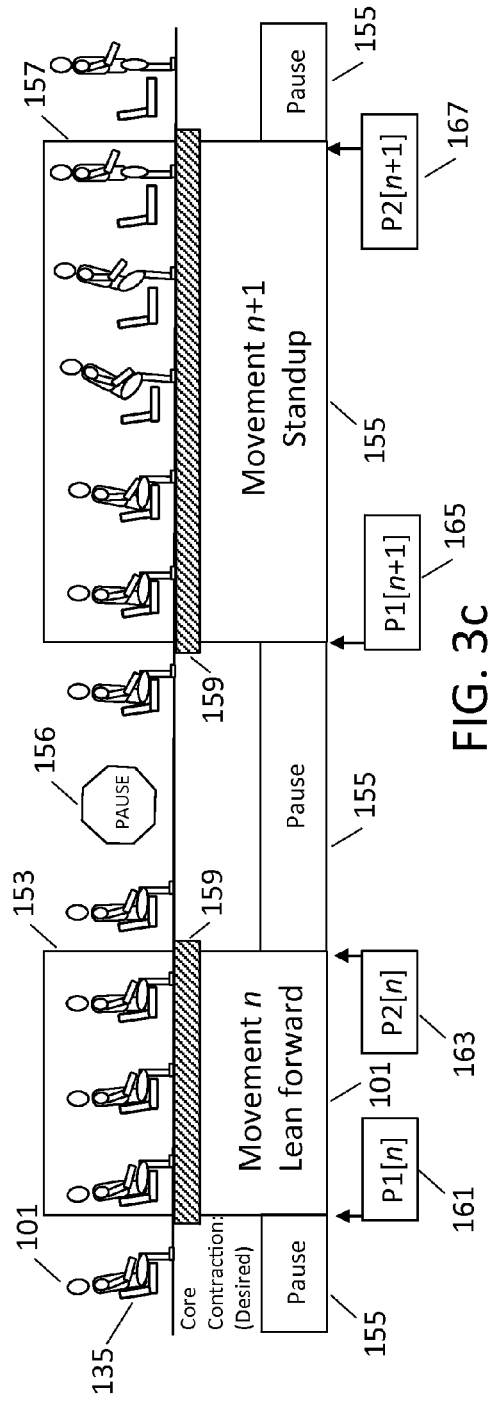

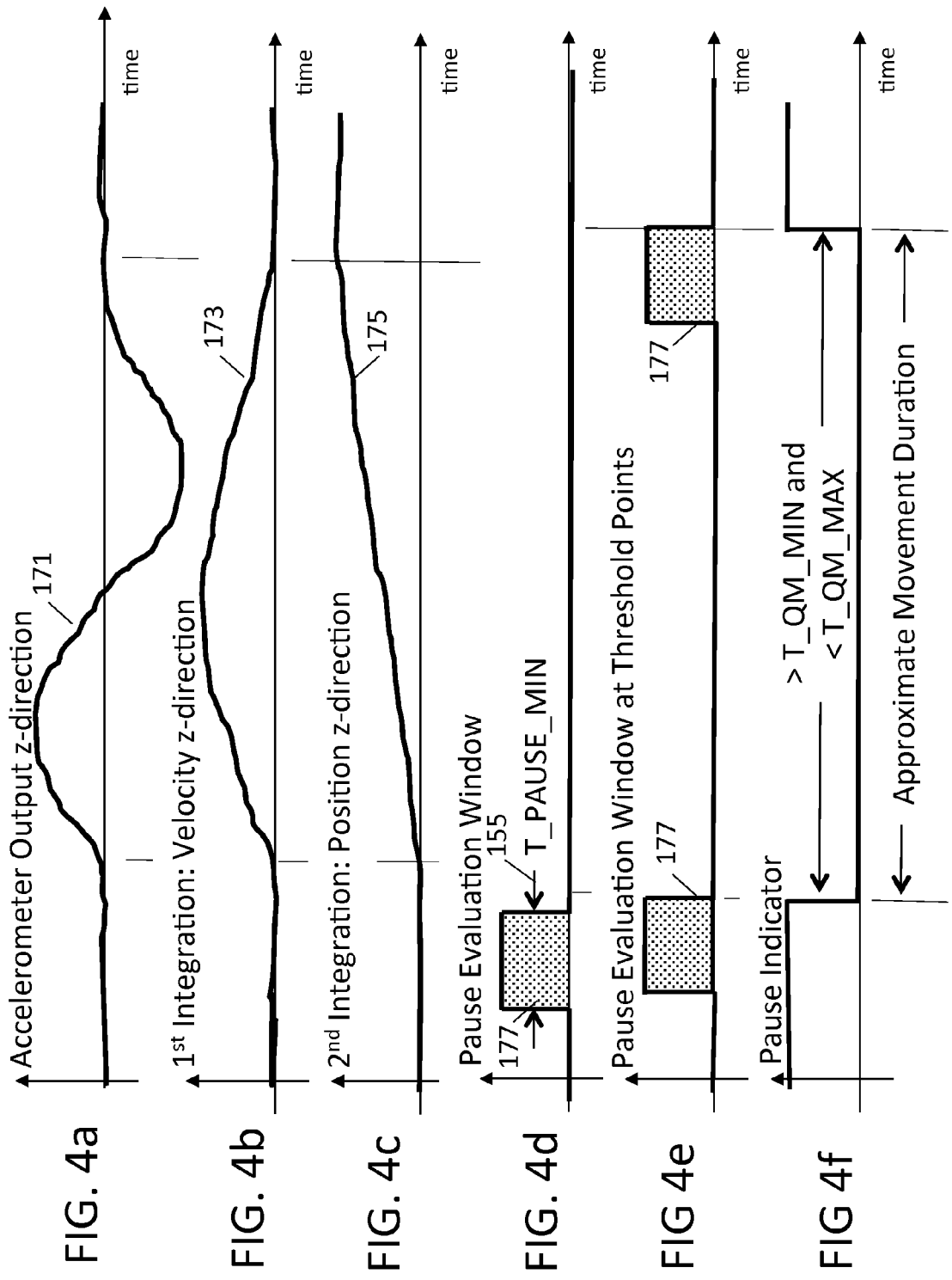

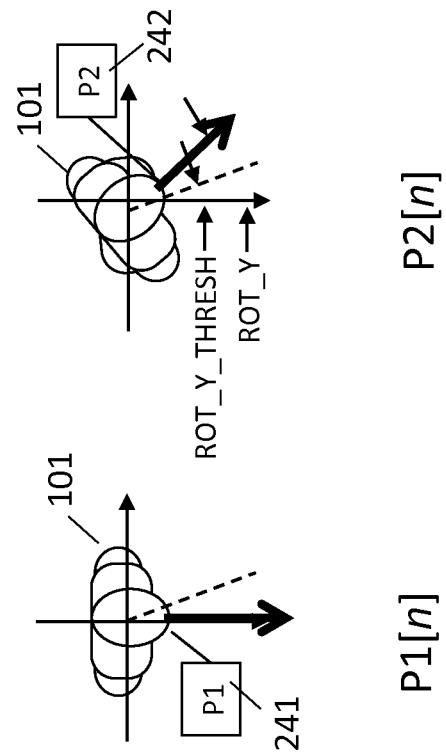
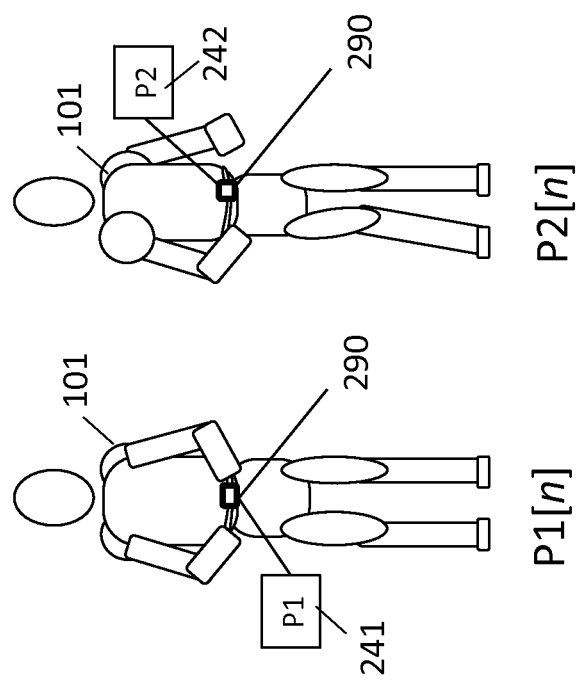
FIG. 5d  FIG. 5c  FIG. 5b  FIG. 5a

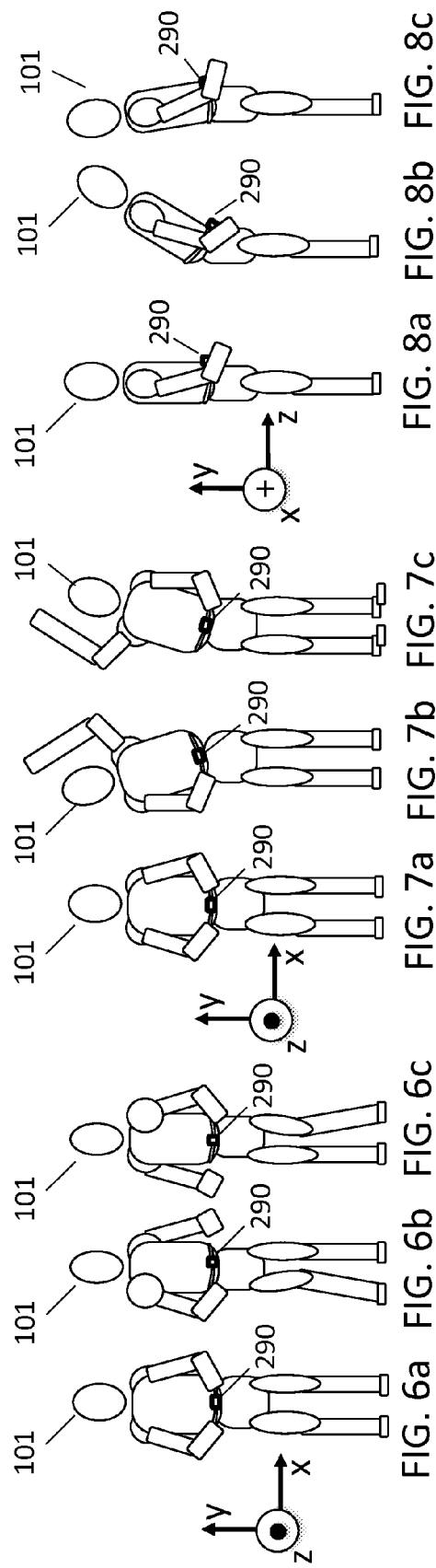

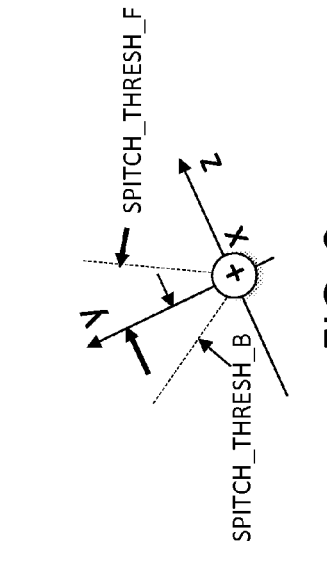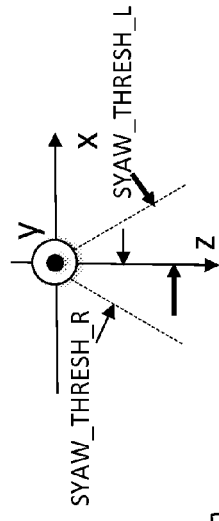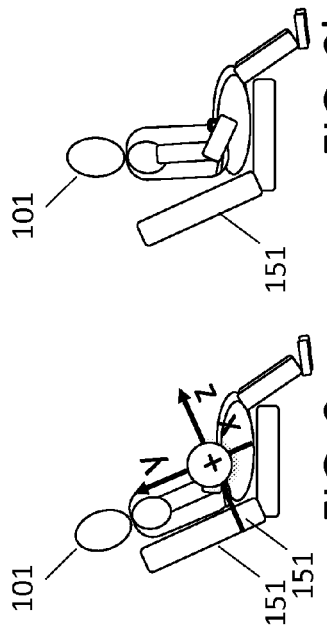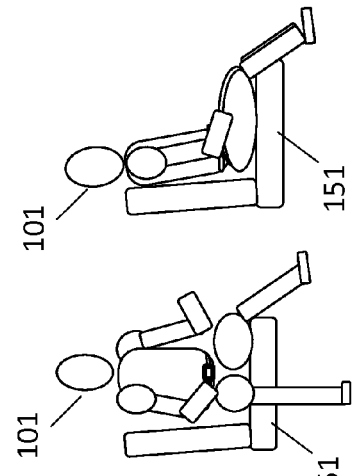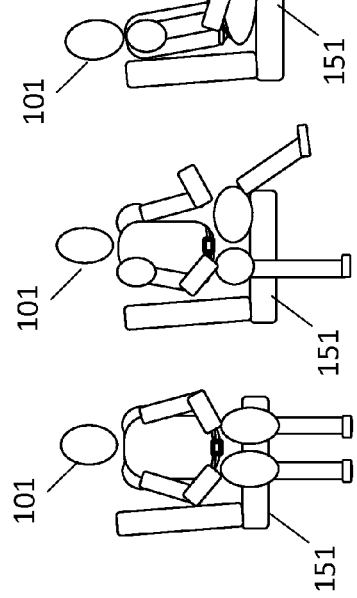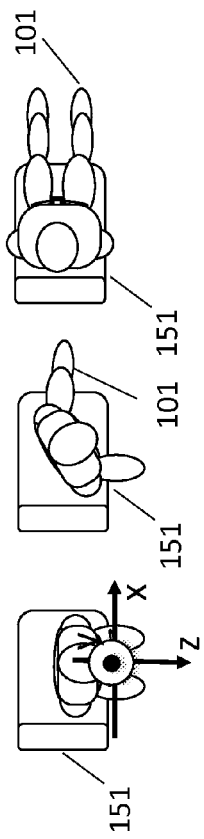

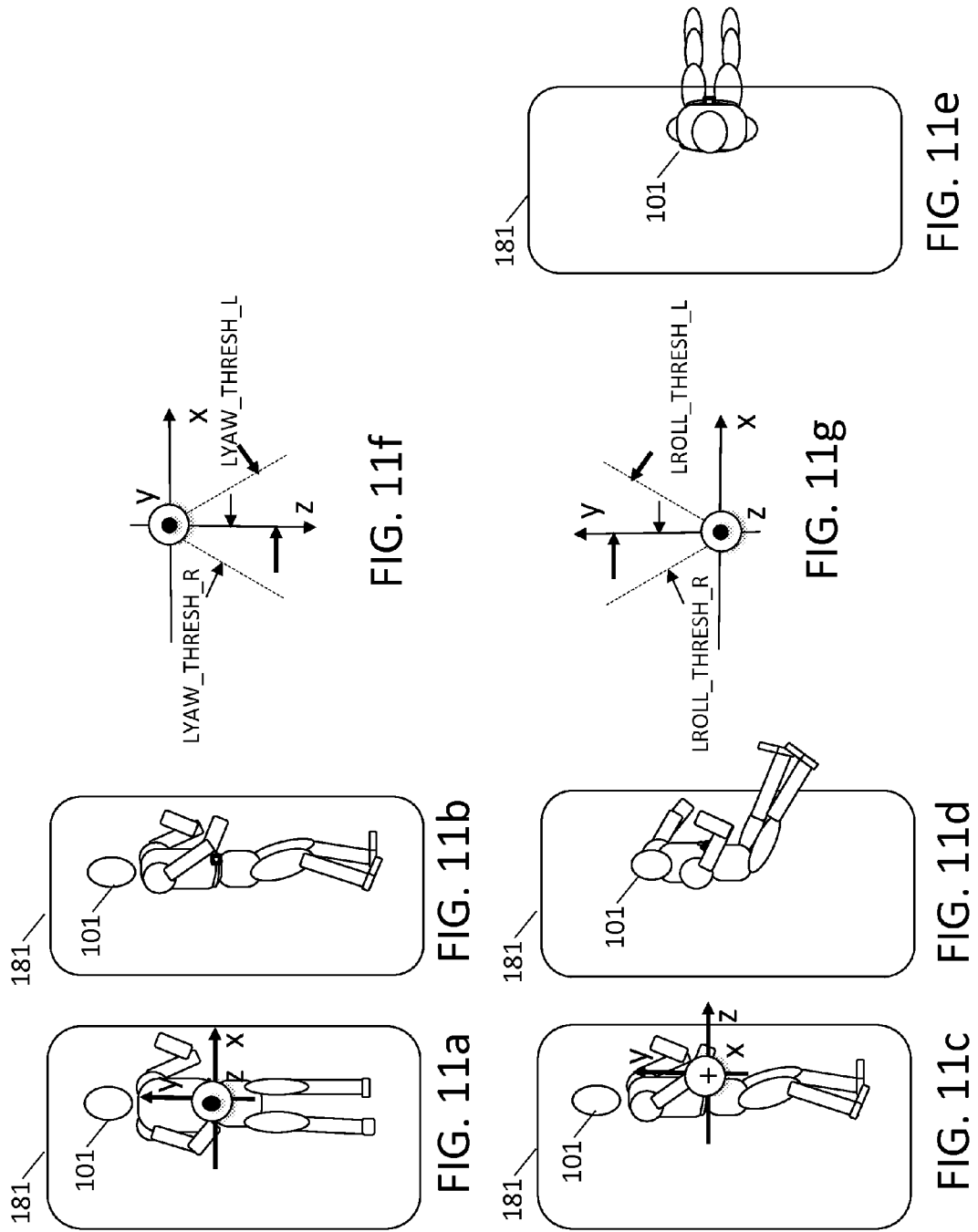

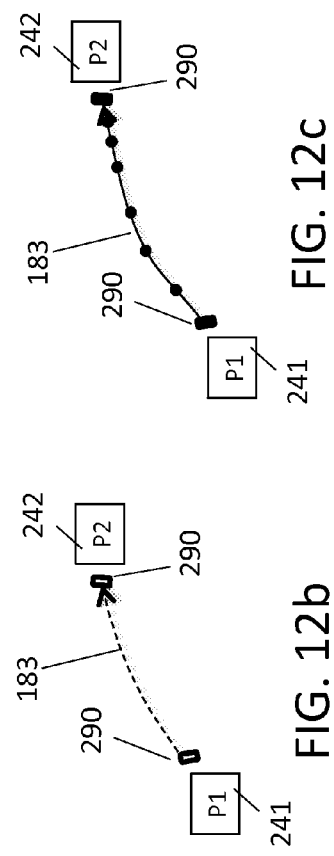
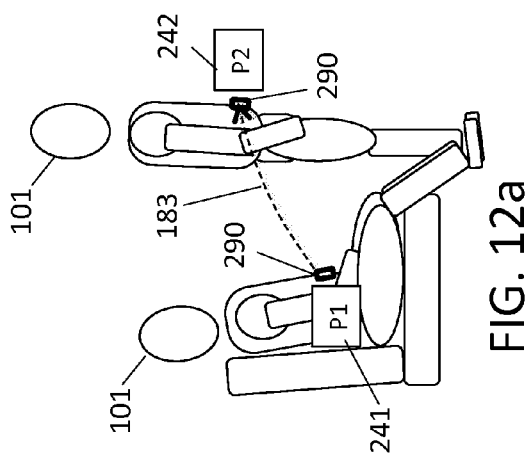
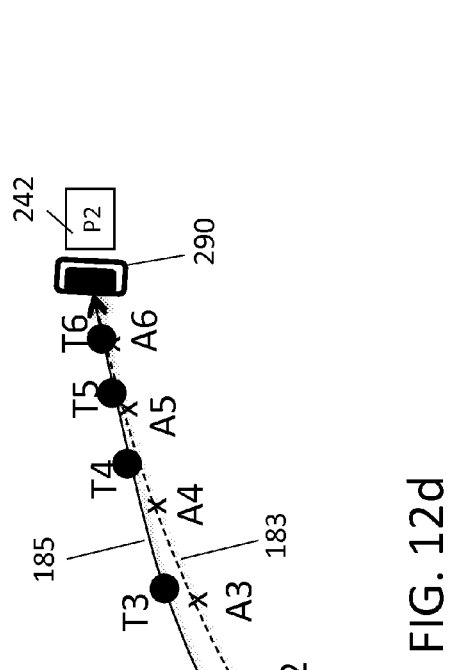
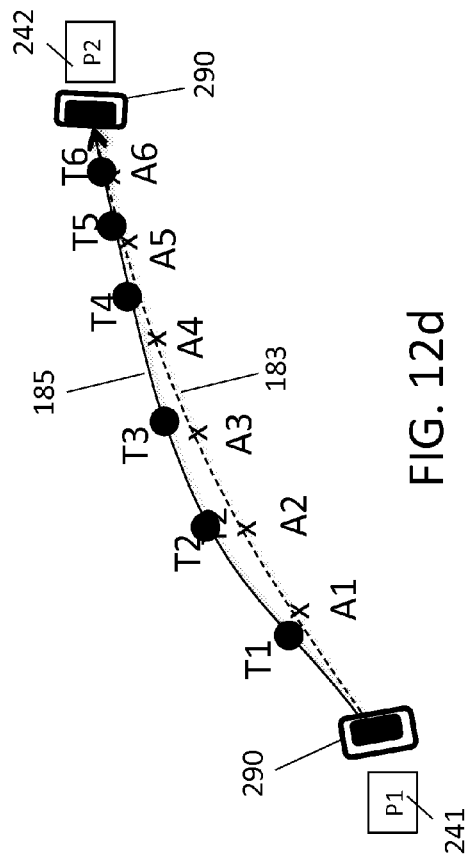

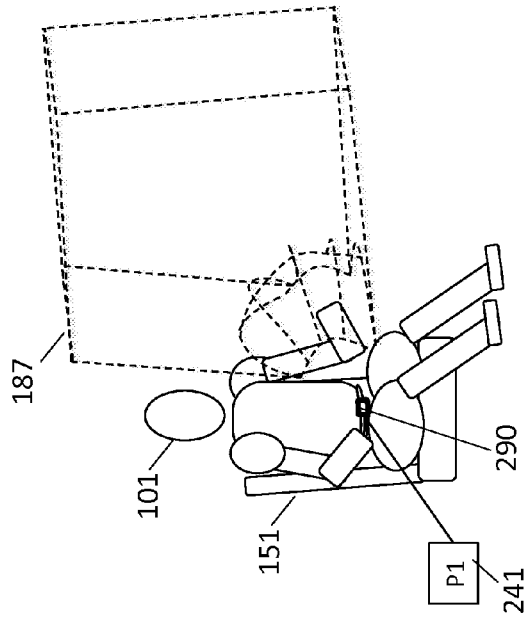
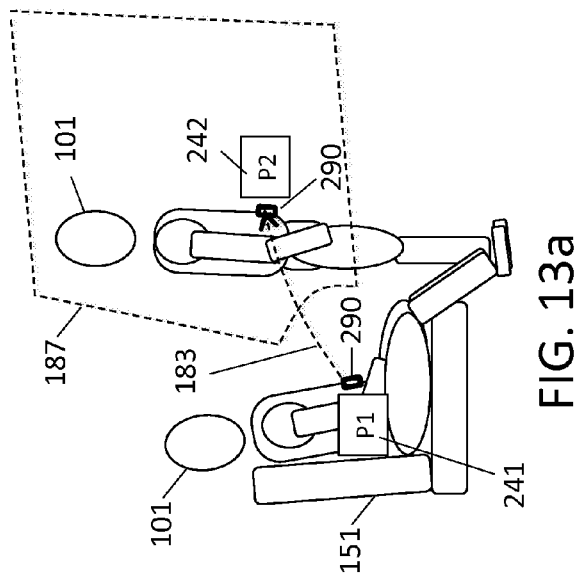
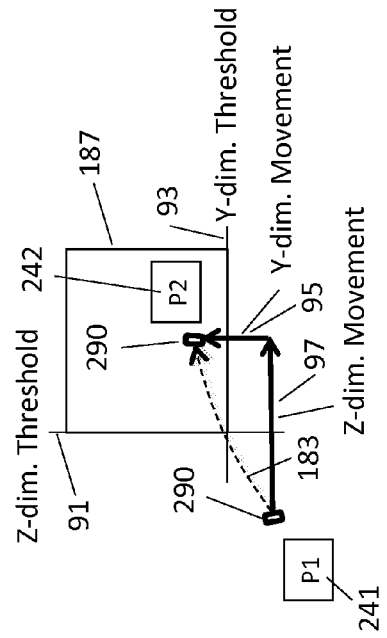
FIG. 13a
FIG. 13b
FIG. 13c

APPARATUS AND METHOD FOR TEACHING AND ALGORITHMS FOR IDENTIFYING QUALIFYING MOVEMENTS

CROSS-REFERENCE TO RELATED APPLICATIONS

This application also claims priority to U.S. Provisional Application No. 62/019,522, entitled "Apparatus And Method For Teaching And Algorithms For Identifying Qualifying Movements", filed Jul. 1, 2014 and U.S. Provisional Application No. 62/027,409, entitled "Apparatus And Method For Teaching And Algorithms For Identifying Qualifying Movements", filed Jul. 22, 2014. This application is a continuation in part of U.S. patent application Ser. No. 14/132,808, entitled "System, Apparatus, And Method For Promoting Usage Of Core Muscles And Other Applications", filed Dec. 18, 2013, which claims priority to U.S. Provisional Application No. 61/739,160, entitled "System For Promoting Usage Of Core Muscles And Other Applications", filed Dec. 19, 2012. The disclosures of U.S. patent application Ser. Nos. 14/132,808, 61/739,160, and 62/019,522 are incorporated herein by reference in their entirety.

FIELD OF THE INVENTION

Embodiments disclosed relate to systems, methods, devices, and algorithms for development of support from core muscles by identifying user movements and by detecting core muscle usage in conjunction with those identified movements. Embodiments also relate to apparatus, systems and methods for discriminating between multiple identified movements, recognizing core muscle activity or lack of it thereof in those identified movements, and providing feedback to the user regarding a correct or incorrect core muscle use, acknowledging a core muscle contraction when appropriate, informing of an inappropriate core muscle contraction, and identifying a movement wherein a core muscle contraction is not performed but could be performed.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

In recent years, there has been explosive growth in the number of portable and handheld devices that include but are not limited to sensors such as accelerometers, gyros, magnetometers, altimeters, and/or pressure sensors. Examples of such devices include smart phones, cell phones, gaming devices, and wearable devices (or wearables).

In gaming devices, tilt or angles of rotation are often tracked and used to control elements of the game. A large number of wearables target health and fitness applications where steps taken and flights of stairs taken by device users are tracked utilizing accelerometers and altimeters.

Inertial navigation is a method utilizing accelerometers, gyroscopes or gyros, and a microprocessor contained on a moving object to continuously calculate device positions utilizing dead reckoning the position, orientation, and velocity of the object. Dead reckoning is the process of calculating the current position by using a previously determined position and advancing that position based on estimated speeds over known elapsed time. A system implementing inertial navigation is self-contained and requires no external references. Inertial navigation has generally been used by aircraft, spacecraft, guided missiles, and ocean craft. Inertial navigation may be used in embodiments of the inventive concepts described in this disclosure targeting systems and devices for the wearables market.

Most health and fitness wearables on the market today may track one or more of the following: steps taken, number of stairs taken, heart rate, movement activity, and sleep patterns. These devices generally utilize accelerometers, altimeters, light sources and sensors, and voltage sensors to sense and detect the parameters they measure and track. Generally, these wearables do not require the combination of position and orientation tracking that may require algorithms utilized in inertial navigation.

SUMMARY OF THE INVENTION

In U.S. patent application Ser. No. 14/132,808, entitled "System, Apparatus, And Method For Promoting Usage Of Core Muscles And Other Applications", filed Dec. 19, 2013, an inventive system is presented including a wearable device which monitors a user's movements for Qualifying Movements, where a Qualifying Movement or QM is a movement for which support from contraction of the core muscles may be beneficial to the lumbosacral junction and lumbar spine. When a Qualifying Movement is identified, the system determines whether or not the Qualifying Movement is protected or not protected based on the status of the user's core before, during, and after the Qualifying Movement. Key objectives of the system include: 1. Having the user contract their core muscles during the time the stress on the lumbar spine and lumbosacral junction is greatest during a Qualifying Movement; and 2. Having the user develop the habit of contracting their core muscles during Qualifying Movements such that they continue this beneficial practice even without the system. In general, if the core is contracted before and during the QM, the QM may be considered protected. However, since it is protecting the lumbosacral junction and lumbar spine when the stress is greatest that matters most, having the core contracted during periods when, for example, the acceleration or deceleration is greater than a threshold may also result in a QM being considered protected. Embodiments may utilize different algorithmic approaches to discriminate between a protected and unprotected qualifying movement. Based on the result of a protected or unprotected qualifying movement, the system may provide a feedback signal to the user. An overall objective of the system is to provide feedback over a period of time to help the user build procedural memory to utilize their core to protect their lumbar spine and lumbosacral junction during QMs. In U.S. patent application Ser. No. 14/132,808, a number of approaches for identifying core contraction using sensors are described.

This invention disclosure describes a system and method to teach and encourage the use of core support during Qualifying Movements. Furthermore, a comprehensive approach including associated algorithms to identify Qualifying Movements is disclosed.

In wearable device applications, there are a number of elements comprising a product definition and implementation: a. Target Behavior: a well-defined high value behavior or sets of behaviors that the system is teaching, encouraging, and tracking; b. Content and Approach for Teaching:

Method or process to teach the desired behavior effectively and to enable someone learning the behavior to quickly begin practicing the desired behavior; c. Wearable Device: Wearable device containing sensors that may include accelerometers, gyros, and other specialized sensors as needed by the application, other supporting electronics including a microprocessor and a communications protocol such as Bluetooth or Zigbee, and a battery, that can be worn comfortably and placed into position on or near the body and removed conveniently; d. Algorithms for Behavior ID (Identification): Algorithms operating on the outputs of the sensors that accurately and consistently identify behaviors and/or movements of the user to compare against the target or desired behaviors; and e. Feedback: Means for providing feedback to the user either positive and/or negative regarding their actual behaviors against target or desired behaviors in order to encourage said target or desired behaviors.

Each of the Items a through e are addressed in U.S. patent application Ser. No. 14/132,808, Items a, c, and e are addressed with a high degree of detail. In this invention disclosure, items b and d are addressed in detail. Item b includes important content for teaching users to identify QMs and a preferred way to move in a deliberate and controlled manner. Item d includes a description of a comprehensive approach for identifying QMs.

The physiology behind core contraction before and during a user qualified movement was described in U.S. patent application Ser. No. 14/132,808. Only a brief summary is presented here. The inner core muscles including the transversus abdominis, multifidus, diaphragm, and pelvic floor are the deepest of the core muscles and may play an important role in supporting the lumbosacral junction and the lumbar spine. The lumbar spine is located near the tail bone and is an area where nerves from the spinal column are distributed to the lower extremities. When basic body movements such as sitting down and standing up are performed without support of the core muscles, stability of the spinal segments comprised of cartilage and vertebrae may be negatively affected. Over time, repeated movements without core support may further reduce the stability of the spinal segments such that when there is movement, the nerves exiting the spine may be pinched or compressed causing pain, weakness, and/or discomfort. Therefore, many disciplines including physical therapy teach support of the lumbosacral junction and lumbar spine through contraction or bracing of the inner core muscles prior to and during movements. As described earlier, we refer to movements for which core support may be beneficial as QMs.

Procedural memory is memory creating a response for particular types of action or actions that result from performing a sequence of activities or movements over and over. When procedural memory is developed for an activity or movement, the desired response can occur in almost a second nature or subconscious way. An important aspect of developing procedural memory for support from the core muscles during QMs is to learn to move in a controlled manner. Controlled movements are, in general, deliberate movements. Moving in a deliberate manner may include breaking complex movements into simple movements with pauses in between. Pauses may be defined as being a substantially negligible movement or substantially negligible rotation in any direction that last at a minimum for fractions of a second. For example, a minimum pause duration may be 250 msec. Pauses may also be considered periods of substantially no movement or non-movement. Throughout this document, pause, no movement, and non-movement are used interchangeably. Pauses help a person maintain balance and control of their body. Pauses facilitate core contraction for lumbar support by allowing a person the opportunity to think to contract their core before making specific movements and to relax their core at appropriate times.

In one embodiment, inertial navigation may be applied in a health and fitness wearable.

In another embodiment, inertial navigation may be applied in a wearable to aid a user in the development of procedural memory for desired movement behavior.

In another embodiment, inertial navigation may be applied in a health and fitness wearable to aid a user in the development of procedural memory for core support during QMs.

In another embodiment, inertial navigation techniques may be applied in a health and fitness wearable to aid in the identification of QMs.

In another embodiment, QMs may be identified from movements that occur between pauses in movement, where a pause may be identified by the system if it lasts longer than a minimum length of time and has a movement or position change in any direction in 3-D space less than a distance threshold, for example one inch and has a change in orientation or rotation of less than a rotation threshold, for example, 10 degrees. Alternatively, a pause may be identified as a number of contiguous sensor outputs or combined sensor outputs or processed sensor outputs (such as position) that have changes in values less than a threshold.

In another embodiment, QMs may be identified from movements with a boundary on either side comprised of a Pause before and a Pause following that are movements longer than a minimum duration of time, example 250 msec, and shorter than a maximum duration of time, for example, 2 sec. The position and orientation of the Wearable Device at the beginning of the movement may be referred to as Position 1 or P1; the position and orientation of the Wearable Device at the end of said movement may be referred to as Position 2 or P2;

In another embodiment, QMs may be identified as a movement following a pause that is evaluated for a duration of time where the position at the beginning of a movement may be referred to as Position 1 or P1 and the position and orientation of the Wearable Device at the end of the duration of time may be referred to as Position 2 or P2.

In another embodiment, QMs may be predominantly simple movements, containing no more than one rotation in one direction. In other embodiments, QMs may be more complex. It is preferable to keep the movements substantially simple to encourage protected QMs.

In another embodiment, targeted QMs may each have a module and an associated QM test. When the QM test is positive, then the associated QM is identified to have occurred. The QM tests for different QMs may be performed in parallel or series or a combination of both.

In another embodiment, QMs may be identified in part, by changes in angle or orientation from P1 to P2 that exceed a threshold. The threshold may be a function of several parameters including state of the user, whether standing, sitting, laying down, or on transportation; direction of the change in orientation; physical characteristics of the user; and any special conditions of the user including their level of fitness and degree of pain, if any, that the user may be experiencing.

In another embodiment, QMs may be identified in part, by changes in position from P1 to P2 that exceed a threshold defined by a volume that may be referred to as the movement being identified. The Threshold Box is referenced to the location and orientation of P1. The Threshold Box shape may be a function of physical characteristics of the user, and any special conditions of the user including their level of fitness; when P2 is located on or within the Threshold Box, a QM for that particular test may be considered positive;

In another embodiment, QMs may be identified in part, by the trajectory from P1 to P2 during a movement matching or being identified as coming close to a trajectory associated with a specific QM.

In another embodiment, QMs may be identified in part, by the previously identified QM.

In another embodiment, changes in position and orientation such as the change from P1 to P2 or the trajectory from P1 to P2 may be evaluated utilizing inertial navigation.

In another embodiment, for advanced users, some QMs may be constructed with two or more QMs in sequence with no pause in between.

In another embodiment, the methods, techniques, and algorithms disclosed for identifying QMs may be applied to an additional device or devices that may work together with the wearable device to identify the changes in position and orientation or trajectory of position change of an additional device or devices providing data that may be used in a complementary manner.

In another embodiment, a QM may be identified as protected when the core is identified as contracted before the start and after the end of the QM.

In another embodiment, a QM may be identified as protected when the core is identified as contracted during a QM.

In another embodiment, a QM may be identified as unprotected when the core is identified as not contracted during a QM.

In another embodiment, a QM may be identified as protected when the core is identified as contracted in different relationships to the QM depending on the specific QM, the fitness level of the user, and the level of core usage of the user.

While there is much emphasis in core strengthening in many disciplines including physical therapy, personal training, yoga, pilates, tai chi, strength training, and many sports including baseball, football, tennis, golf, and volleyball, there is no convenient way or teaching aids available to teach core usage in every day movements and activities. Many physical therapy and personal training strategies attempt to teach a client to use their core during exercises, with the objective of getting clients to develop the habit of using their core in relationship to their movements outside of the sessions. Many therapists and trainers wish to have their clients develop procedural memory for using their core to protect their lumbosacral junction and lumbar spine during movements. The development of procedural may occur through frequent repetition of a sequence of actions. However, it is difficult to enable the development of procedural memory for support from the core muscles due to the absence of teaching tools and systems that are affordable, convenient to use, portable, and suitable for continuous use or near continuous use outside of therapy sessions.

While sensor use has become ubiquitous for gaming and wearable applications, algorithms which operate on the data provided by the sensors must be developed to meet the requirements for each application. Algorithms provide translation of sensor data resulting from movements of the sensors into input parameters for other algorithms or portions of algorithms. These algorithms may be part of a larger program code that responds to the sensor data as input data and provides a desired response or a desired combination of responses. Responses may include, for example, having an icon or avatar move on the display in a game application, identifying a walking step in a movement tracking device that may be input to a counting unit for immediate or delayed reporting to the user, and identifying a heart beat in a heart rate monitor which may be counted to report to the user the number of their heart beats per a unit of time on a visual display.

An algorithm may run on a microprocessor or digital signal processor and programming code efficiency is desirable to minimize power consumed by the electronic devices which may be battery operated. Power consumption is an important consideration, requiring efficient and optimized or fairly optimized programming code. Algorithms must be reliable and effective in identifying and interpreting movements of the sensors as intended by the application. Applications have different and varying degrees of requirements for coverage of the types of movements that may need to be identified. Examples of differing requirements include the accuracy with which one movement may be distinguished from another (right rotation versus move down) and the accuracy of the parameter being identified (movements of one inch versus 5 inches). In some applications, clear requirements may be identified, for example, by governing entities such as the Food and Drug Administration. In other applications, accuracy requirements may be arbitrarily set by a product developer since no hard and fast requirements may be available. In cases of the latter, user experience may determine how and where accuracy requirements may be set for detected movements. If the algorithms are not accurate and movements that should be identified are missed, or if movements are incorrectly identified at a rate that is too high, the device or system may lose credibility with the user and the user may not have confidence in the device or system. Devices or systems with limited or little credibility may also lose utility for the user as the user loses confidence in the accuracy of the device or system. When a user loses confidence in the reliability of a system, they user is likely to stop using the device and system.

In order to implement a portable and compact system that encourages a user to develop procedural memory for support from the core muscles of the lumbosacral junction, it is desirable and most convenient for the user to implement the system with the fewest number of system device components. In U.S. patent application Ser. No. 14/132,808, an inventive system is described utilizing one wearable device. A comprehensive set of algorithms is needed to identify Qualifying Movements based on low cost sensor technologies residing on such a device. The algorithms should identify an adequate number of every day or functional movements that may be considered QMs, and identify them consistently and with an adequate degree of accuracy to meet the expectations of most users.

A comprehensive method to teach users to contract their core to protect QMs is also needed. Connecting this teaching method with a device and system to provide immediate and continuous feedback during training and practice sessions and in situ during movements performed during every day activities with effective QM Identification would be beneficial to users, as well as therapists, trainers, and others teaching regular contraction of the core during QMs to clients and patients.

A system for developing procedural memory for core support of the lumbosacral junction during QMs has been disclosed and described in U.S. patent application Ser. No. 14/132,808. In this patent application, a comprehensive approach for teaching and identifying QMs utilizing in part, inertial navigation is described. The presented concepts can be utilized in a system with programmability which may allow a system to be customized and optimized for the level of core usage of the user, as well as the user's overall fitness and conditioning levels.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIG. 3a illustrates a user moving to a stand position from a sit position.

FIG. 3b illustrates the user in FIG. 3a breaking the movement into two simple movements with a pause in between the two movements.

FIG. 3c illustrates the user of FIG. 3b with more detailed description of the user's movements, examples of position designators P1 and P2, and indications of desired core contraction timing.

FIG. 4a illustrates an example accelerometer output vs. time during a user sitting to standing movement.

FIG. 4b illustrates the corresponding velocity vs. time during a user sitting to standing movement.

FIG. 4c illustrates the corresponding relative position vs. time during a user sitting to standing movement.

FIG. 4d illustrates a Pause Evaluation Window indicating T_PAUSE_MIN.

FIG. 4e illustrates the position of the Pause Evaluation Window when the user's movement exceeds the threshold defined for a Pause during a user sitting to standing movement.

FIG. 4f illustrates one example of how the Pause Indicators may identify the duration of a Movement.

FIG. 5a depicts a front view of a user with the wearable device in the P1 position while standing.

FIG. 5b depicts a front view of a user with the wearable device in the P2 position after rotating to the left while standing.

FIG. 5c depict the top view of the user of FIG. 5a.

FIG. 5d depict the top view of the user of FIG. 5b.

FIG. 6a depicts a front view of a user while standing.

FIG. 6b illustrates a user rotating to the left while standing.

FIG. 6c illustrates a user rotating right while standing.

FIG. 6d illustrates thresholds for Rotation Thresholding for Y-axis rotations while standing.

FIG. 7a illustrates a front view of a standing user.

FIG. 7b illustrates a front view of a standing user leaning to the left while standing.

FIG. 7c illustrates a front view of a standing user leaning to the right while standing.

FIG. 7d illustrates the associated thresholds for Rotation Thresholding for Z-axis rotation while standing.

FIG. 8a illustrates a side view of a user.

FIG. 8b illustrates a side view of a user leaning forward while standing.

FIG. 8c illustrates a side view of a user leaning back while standing.

FIG. 8d illustrates the associated thresholds for Rotation Thresholding for X-axis rotation while standing.

FIG. 9a depicts a side view of a user in a seated position.

FIG. 9b illustrates a side view of a user leaning forward from a seated position.

FIG. 9c illustrates the associated thresholds for Rotation Thresholding for X-axis rotation while seated.

FIG. 10a depicts a front view of a user in a seated position.

FIG. 10b illustrates a top view of the user shown in FIG. 10a.

FIG. 10c illustrates an angled view of the user rotating 45 degrees to the left while sitting.

FIG. 10d illustrates a top view of the user shown in FIG. 10c.

FIG. 10e illustrates a side view of the user after rotating 90 degrees to the left while sitting.

FIG. 10f illustrates a top view of the user shown in FIG. 10e

FIG. 10g illustrates the associated thresholds for Rotation Thresholding for Y axis rotation while seated.

FIG. 11a illustrates a user laying down in bed in an X-Y plane.

FIG. 11b illustrates a user rotating to the left in bed.

FIG. 11c a user laying down on a side position in the Y-Z plane.

FIG. 11d illustrates a user rotating about the Z-axis.

FIG. 11e illustrates the user sitting on the bed after rotating 90 degrees about the Z-axis.

FIG. 11f illustrates the associated thresholds for Rotation Thresholding about the Y-axis while the user is in a horizontal orientation shown in FIGS. 11a and 11b.

FIG. 11g illustrates the associated thresholds for Rotation Thresholding about the Z-axis while the user is in a horizontal orientation shown in FIGS. 11c, 11d and 11e.

FIG. 12a illustrates a side view of a user moving from the sit to stand position.

FIG. 12b illustrates an actual trajectory of the wearable device from a sit position P1 to a stand position P2.

FIG. 12c illustrates a target trajectory of the wearable device from a sit position P1 to a stand position P2.

FIG. 12d illustrates an overlay of the actual trajectory and the target trajectory for the sit-to-stand movement with the target trajectory scaled to coincide with the actual trajectory at the endpoints.

FIG. 13a illustrates Position Thresholding with an embodiment of a 2-dimensional Threshold Box for the QM of standing from a seated position FIG. 13b illustrates Position Thresholding with an embodiment of a 3-dimentional Threshold Box for the QM of standing from an angled seated position.

FIG. 13c illustrates an embodiment of the Threshold Box in the Y-Z plane.

DETAILED DESCRIPTION

In U.S. patent application Ser. No. 14/132,808, an inventive device and system is described, one embodiment of which enables real-time tracking of the inner core muscles. The inventive device and system encourage the development of procedural memory for usage of the core muscles during Qualifying Movements (QM) which are defined as movements for which contraction of the core muscles may be beneficial in supporting the lumbosacral junction and lumbar spine.

In this present disclosure, a comprehensive approach for algorithms for QM Identification or QM ID is described. An important inventive element in this disclosure is the definition of basic movements that are fundamentally simple for a user to execute that are also easily identifiable by a processor using the movement outputs of low-cost sensors. The core contractions can be detected with a core sensor and the processor can detect core contractions during QMs based upon the outputs of the movement and core sensors. We refer to QMs with appropriate core contraction support as protected QMs or simply protected movements.

Figure 1B:
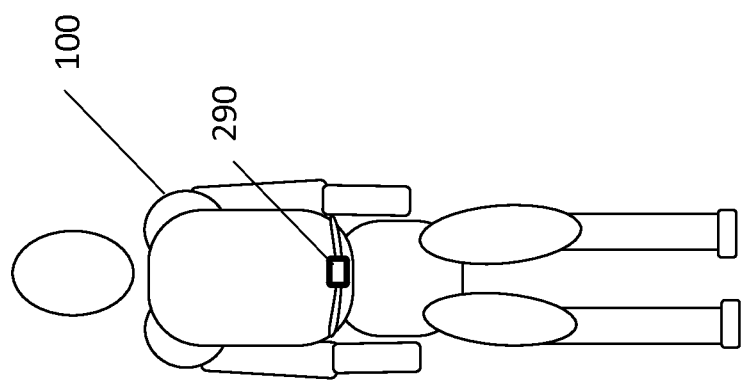
FIG. 1b illustrates a block diagram of an embodiment of the wearable device showing a PCB containing a 3-axis accelerometer and a 3-axis gyro.
Figure 1A:
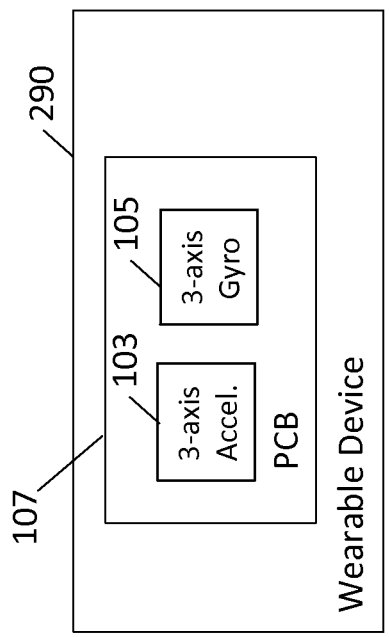
FIG. 1a illustrates a front view of a user wearing an embodiment of the inventive device worn by a user.

With reference to FIG. 1a, an embodiment of the wearable device 290 described in U.S. patent application Ser. No. 14/132,808 is shown worn on a user 101 at the preferred position between the naval and the groin areas of the user's torso. This position for the wearable device 290 can be comfortably worn by the user 101 and can provide accurate movement detection of the user 101. However, in other embodiments, the wearable device 290 can be worn on other areas of the user's body.

With reference to FIG. 1b, an embodiment of a 3-axis accelerometer 103 and a 3-axis gyro 105 are shown conceptually on a printed circuit board (PCB) 107 as they may be included inside the wearable device 290. Other sensors may also be included in the device 290.

Figure 1C:
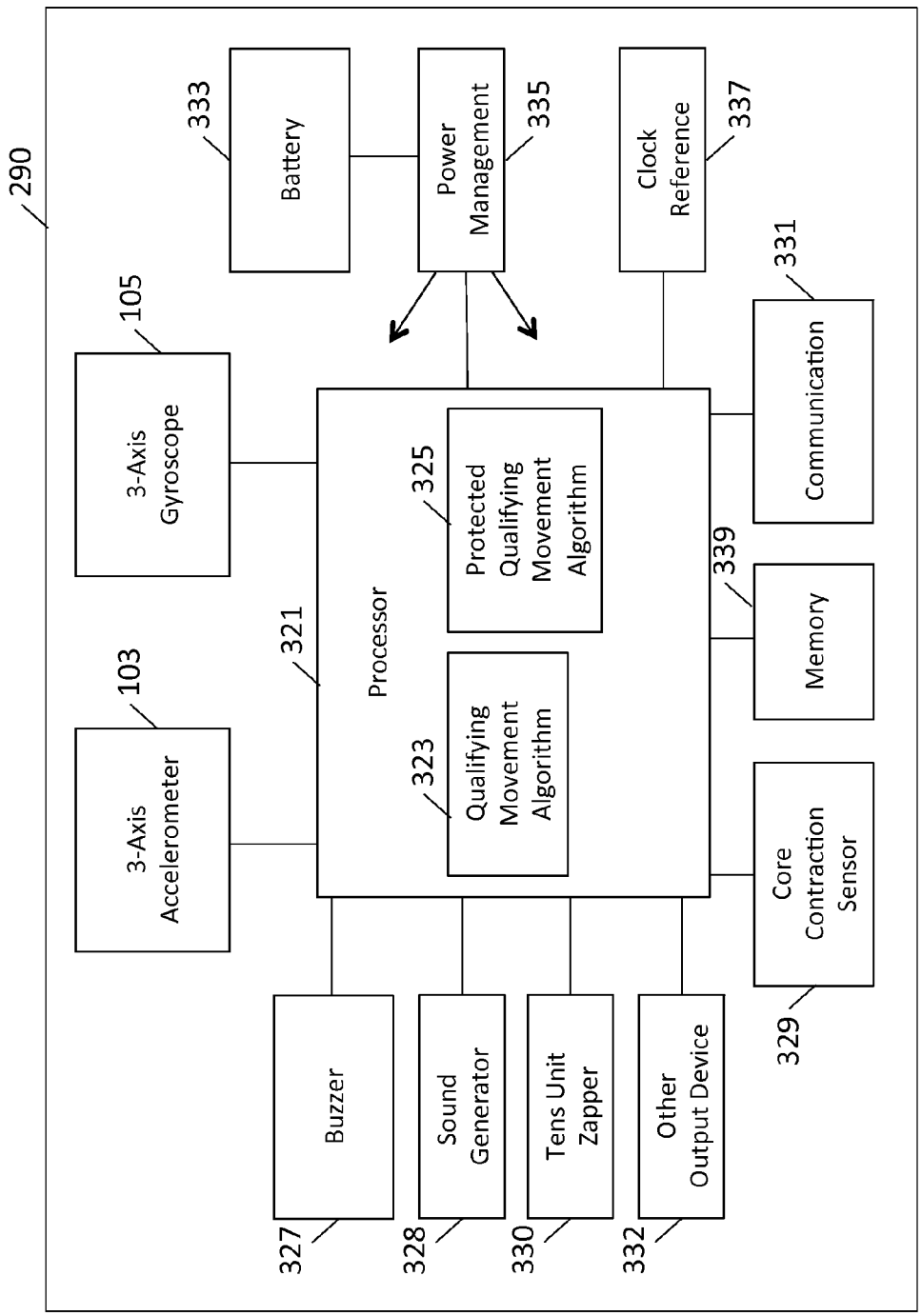
FIG. 1c illustrates a block diagram of an embodiment of the inventive system components.

With reference to FIG. 1c, a block diagram of an embodiment of the wearable device 290 is illustrated. As discussed, the 3-axis accelerometer 103 and the 3-axis gyroscope 105 are coupled to the processor 321 and a core contraction sensor 329 can also be coupled to the processor 321. The processor 321 can include a qualifying movement algorithm 323 and a protected qualifying movement algorithm 325 which can be software stored in a memory 339 or firmware. The movement signals from the 3-axis accelerometer 103 and the 3-axis gyroscope 105 can be processed by the qualifying movement algorithm 323. Output signals from the qualifying movement algorithm 323 and contraction signals from core contraction sensor 329 can be processed by the protected qualifying movement algorithm 323.

In an embodiment, the qualifying movement algorithm 323 and the protected qualifying movement algorithm 325 can be updated as improvements or changes are made to these algorithms. In an embodiment, the algorithm updates can be transmitted to the wearable device 290 through a communications 331 port which can provide network communications with other computing devices. For example, in an embodiment, the system can obtain software or firmware downloads from servers through an internet connection. The processor 321 can also be coupled to various output devices which can provide information to the user which can include one or more of: a buzzer 327, a sound generator 328, a transcutaneous electrical nerve stimulator (TENS) zapper 330 or other output device(s) 332. The output devices 327-332 can emit output signals to the user that indicating correct core contractions during QMs or incorrect core contractions. In different embodiments, different output devices can be selected. For example, a buzzer 327 or sound generator 328 can be useful at home, but these audio output devices may not be appropriate at an office where other employees will hear the output sounds. A TENS zapper 330 can be coupled to a surface area of the user's body and provide a nerve stimulation to indicate correct core contractions during QMs or incorrect core contractions. Alternatively, an output device such as a light or visual output may be useful providing feedback to users in areas where others noise can be disruptive to others.

The processor 321 can also be coupled to a communications device 331 that can transmit information to other devices through a wired or wireless communications connection, for example the communications device 331 can be a Bluetooth device that provides wireless communications to other devices. A battery 333 can be coupled to a power management module 335 which can control the distribution of electrical power to the system components. The battery 333 can be rechargeable and capable of being charged with a charger. The processor 321 can also be coupled to a memory 339 which can store information about the user(s) and record user movement and core contraction data. The system can also include a clock reference 337 which can provide a system reference clock to the processor which may also be used to derive sampling clocks for the sensors 103, 105. If the system has a minimum of intermittent access to date and time information, for example through a cellular system, the clock reference 337 may be utilized in an algorithm using such date and time information so that recorded movements and core contractions can be stored with time stamps.

Inertial navigation methods may utilize output signals from the accelerometers 103 and gyros 105 in a device 290 to calculate positions, orientations, movement trajectories, and rotations of the device 290 and the user in 3-dimensional or 3-D space. Various different methods can be used to calculate the user movement. For example in an embodiment, starting at a first point in 3-D space, the sensor outputs from the accelerometers 103 and gyros 105 may be combined and processed by qualifying movement algorithm 323 running on a processor 321 to calculate estimates of the orientation and the direction, speed, and rotation of a wearable device 290 and a user over a known interval of time to a second point. These estimates of orientation, direction, speed, and rotation over the known interval of time allow the system to calculate estimates for orientation, position, and rotation of the wearable device 290 and user with respect to the starting point. During the next interval of time, new data is added to derive a new estimate of orientation, position, and rotation with respect to the second point. By repeating this process, the trajectory of the orientation, position, and rotation of the device in 3-D space may be estimated by the processor 321.

Figure 2:
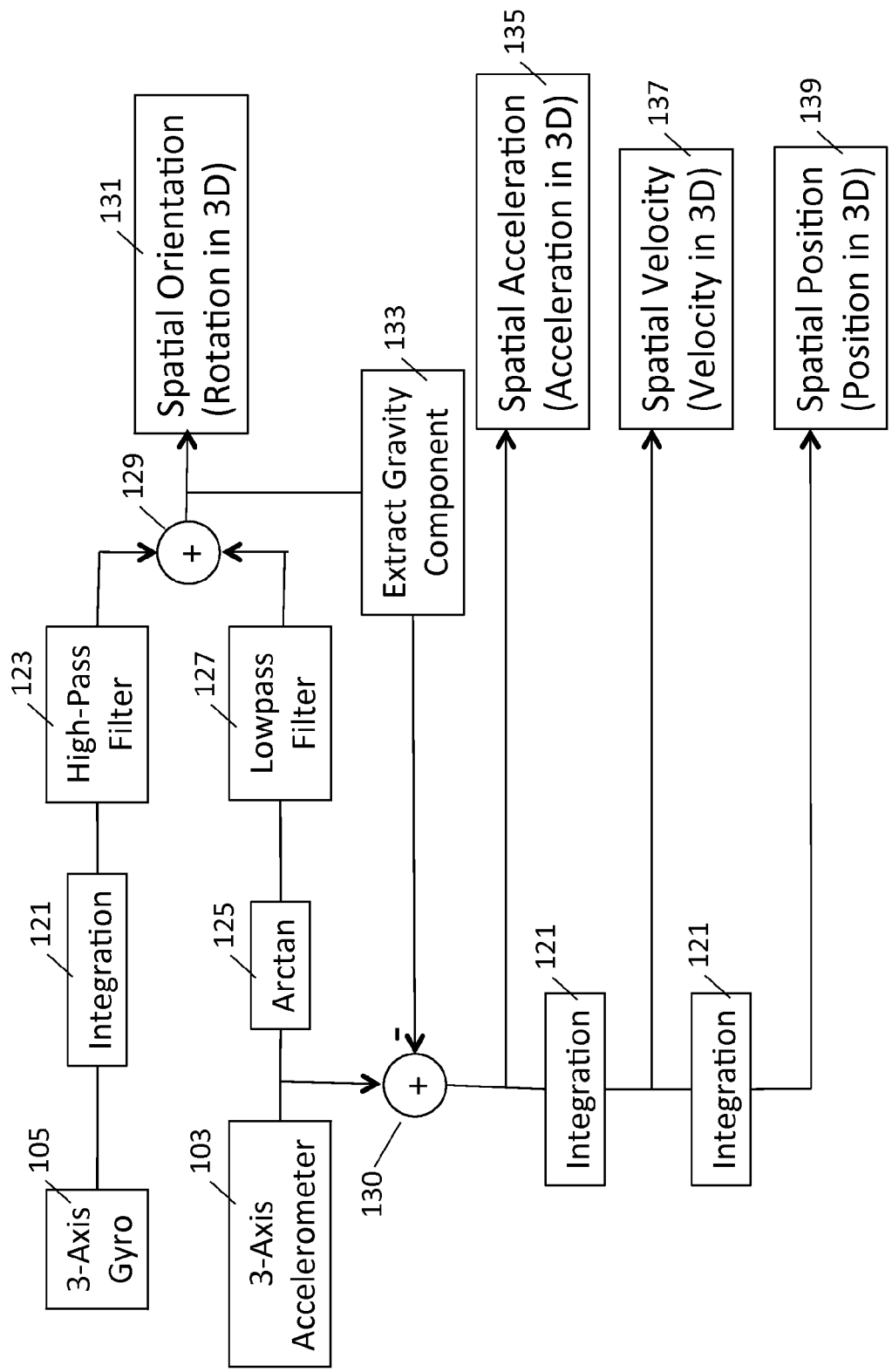
FIG. 2 illustrates an embodiment of a simplified signal processing block diagram of sensor fusion where accelerometer and gyro data are combined to calculate changes in position and orientation.

In FIG. 2, an embodiment of a signal processing path to calculate orientation and changes in movement and rotation of a user utilizing signals from the accelerometer 103 and gyro 105 is shown. This exemplary diagram is simplified for illustrative purposes. For example, the arctan function 125 is defined in two dimensions while it is shown with a 3-D input from the accelerometers 103. Additional complexity is required to address issues associated with extending the signal processing into three dimensions. Nonetheless, key concepts underlying the functionality are included in this description and the inventive system is designed to detect movement, orientation, position and rotation in three-dimensional space.

The structure of the signal path shown in FIG. 2 is sometimes referred to as sensor fusion as the outputs of different types of sensors are combined to achieve an improved result. Sensor fusion techniques are commonly used in applications employing accelerometers and gyros and other sensors in order to overcome shortcomings of the individual sensors such as offsets and the impact of gravity on accelerometers. The output of the system is a spatial orientation 131 in three dimensions.

The output signals from the 3-axis gyro 105 provide rotational velocity signals for the wearable device 290. Since the output of the gyro 105 is angular velocity, the gyro 105 output must be integrated with an integration processor 121 in order to determine orientation. The output signals from the accelerometers 103 may also be used to calculate spatial orientation. The accelerometer 103 output signals can be passed through the arctan function 125 to compute the spatial orientation. The low frequency characteristics of integrated gyros 105, in practice, tends to be noisy or have drift; while the high frequency characteristics of accelerometers 103, in practice, tends to be noisy. Thus, by passing the gyro 105 output signal result through a high-pass filter 123 and the accelerometer 103 output signal result through a lowpass filter 127 and adding 129 the two subsequent output signal results together can produce a measure of spatial orientation 131 of the wearable device with preferred high and low frequency characteristics.

Gravity results in a constant acceleration vector toward the earth, creating a bias gravity component 133 in the accelerometer 103 output. The orientation calculation result may be utilized to identify the acceleration component in the direction of gravity. This component 103 in the direction of gravity may be subtracted from the accelerometer 103 output in order to remove the bias component due to gravity. This is shown in FIG. 2 as the subtraction 130 of the spatial orientation 131 output from the accelerometer 103 output. The result is spatial acceleration 135 or acceleration in three dimensions without the gravity component 133 of acceleration due to gravity. The spatial acceleration 135 result may be integrated 121 to calculate spatial velocity 137 or velocity in three dimensions. And finally, the spatial velocity 137 may be integrated 121 to determine the spatial position 139.

Practically speaking, manufacturing variations in the sensors can result in offsets and gain errors that may need to be addressed by the wearable device utilizing techniques such as calibration, compensation, filtering, and auto-zeroing or similar methods to remove direct current (DC) offsets as one skilled in the art would understand. Other methods may be utilized to address these and other practical issues.

An important aspect of developing procedural memory for (contraction) support of the core muscles during QMs is to practice and learn to move in a controlled manner. Controlled movements may in general, be characterized as deliberate movements. Moving in a deliberate manner may include breaking complex movements into a plurality of simple movements with pauses in between. Pauses may be fractions of a second in duration (for example, as short as 250 msec.) and may have negligible movement or rotation in any direction. For example, a movement of less than one inch in any direction and less than 10 degrees of rotation on any axis over the pause duration can be a negligible movement that can be identified by the system as a pause. Pauses can help a person maintain balance and control of their body. Pauses can also facilitate core contraction for lumbar support by allowing a person the opportunity to think to contract their core during the pauses before making specific movements and to relax their core at the appropriate times.

Referring to FIG. 3a, user 101 body positions are depicted in a time-lapse manner (from left to right) standing up from a leaning deep back position in a chair 151. In FIG. 3b, the user 101 movement from leaning back in a seat to standing up is shown where the movement is broken into two movements; a first lean forward movement 153 of a user 101 from a position against the back of the chair 151 to the edge of the chair 151, pausing as shown by the Pause sign 155, then second stand up movement 157 where the user 101 moving from the edge of chair 151 position to the Stand position. In an embodiment, both the movement 153 leaning forward from a deep incline to sitting upright, and the movement 157 sitting upright to the Stand position are considered QMs. It may be desirable to protect both movements 153, 157 with a contracted core prior to and during each of the movements 153, 157. If the core is contracted during the movement 153, 157, the movements can be considered to be protected QMs. If movement 153 leaning forward from a deep incline to a sitting upright position is performed slowly, it may not be considered a QM.

In FIG. 3c, the user movements are shown with some additional features. The user's Movement n (first lean forward movement 153) and Movement n+1 (second stand up movement 157) are indicated by enclosure boxes. Both movements 153, 157 can have a boundary on either side comprised of Pauses 155. The positions P1 and P2 for Movement n 153 are depicted as P1[n] 161 and P2[n] 163, respectively. These indicate the position and orientation of the wearable device at their respective instants, that is, P1[n] 161 can indicate the user 101 position and orientation at the very start of Movement n 153, following the Pause 155; and P2[n] 163 can indicate the user 101 position and orientation at the end of Movement n 153, just before the following Pause 155. It may be sufficient to identify the moment of occurrence of P1[n] 161 as being roughly around the start and the moment of occurrence of P2[n] 163 as being roughly around the end of Movement n 153.

Another feature of FIG. 3c is the cross-hatched bars 159 under the user 101 indicating examples when the user 101 may contract their core in order to identify the movements 153, 157 as protected movements. The cross-hatched bars 159 are designated as Core Contraction (Desired). In these examples, the cross-hatched bars 159 begin during the Pause 155 and prior to the movements 153, 157. The cross-hatched bars 159 also indicate that the core stays contracted throughout the movements 153, 157, and continues through the start of the following Pause 155. The areas that do not have the cross-hatched bars 159 are the pauses 155 that do not need core contraction.

Practical limitations may result in ambiguity as to precisely when the movement begins and ends. These limitations include the accuracy with which movements can be identified by algorithms and variations in the way movements are performed and combined in everyday life. Furthermore, pauses before qualifying movements are often followed by slow movements prior to qualifying movements and precisely defining the instant when one type of movement or non-movement ends and another begins may be difficult and of little value. The lean forward movement from the first Pause 155 to the second Pause 155 may illustrate a movement that may be conditionally considered a QM. Examples of conditions that may result in this movement being considered a QM include the user being in an active episode of back pain and the movement being performed quickly. This example illustrates the flexibility of the system to be optimized for different user conditions and different use conditions.

An example of identification of Pauses and Movements can be based on the output of an accelerometer. The concepts in this example may be extended to more complex sensor configurations in 2 and 3-dimensions. However, for a simplified explanation, FIGS. 4a-4c, illustrate acceleration, velocity, and position in only the Z direction. An example of the changes in output of an accelerometer over time is shown in FIG. 4a for acceleration in the z-dimension 171 which would correspond to an acceleration movement of the wearable device in a forward horizontal direction. This forward movement may be part of a sit-to-stand movement. The initial positive acceleration is caused by the initial forward acceleration and the user slowing before assuming a standing position causes the subsequent deceleration. The first integration of the accelerometer output over time is velocity in the z-dimension 173 shown in FIG. 4b. The velocity increases until the middle of the movement and then slows. The second integration of the accelerometer output over time illustrates position of the wearable device in the z-dimension 175 is shown in FIG. 4c. The starting limit on the integration for velocity and the integration for position may begin where the accelerometer output becomes non-zero associated with the movement being analyzed. The double integration of acceleration over a given time period is equal to the change of position in the direction of the acceleration over the period of integration. Therefore, by performing a double integration of the z-dimension accelerometer output over a given period of time, the change in position in the z-dimension 175 over that period of time may be calculated. In the illustrated example, the z-direction movement can be a movement from a seated leaning forward position in a chair to a standing position followed by a pause where the wearable device moves forward and then stops.

In FIG. 4d, the minimum period for a Pause 155 is shown as an Evaluation Time Window 177 of width T_PAUSE_MIN. An example value for T_PAUSE_MIN is 250 msec. The accelerometer output (shown in FIG. 4a) within the time window may be double integrated to determine the movement in the z-dimension (shown in FIG. 4c) over T_PAUSE_MIN. If the distance moved over T_PAUSE_MIN is less than a minimum movement threshold D_MOVE_MIN, for example, one inch, a valid Pause in the user's body movement may be identified by the processor. When there is substantial movement by the user which may qualify as a QM, the time window 177 will move to the right along the time axis and at some point the time window 177 will be positioned on the user's movement data such that the double integration of the accelerometer output (the calculated user movement) will be greater than D_MOVE_MIN which can indicate the start of a QM.

With reference to FIG. 4e, both the time windows 177 location when the movement over time period T_PAUSE_MIN first exceeds D_MOVE_MIN and when the movement over time period T_PAUSE_MIN decreases below D_MOVE_MIN are shown in FIG. 4e as the Evaluation Windows 177 at the Threshold Points. One way to estimate the Approximate Movement Duration is to utilize the Threshold Points of FIG. 4e and to begin at the start of the T_PAUSE_MIN window first when the movement first exceeded D_MOVE_MIN, and end at the end of the T_PAUSE_MIN window when the movement was less than D_MOVE_MIN as shown in FIG. 4f. If the Approximate Movement Duration is longer than the minimum period for a QM of T_QM_MIN, and shorter than a maximum period of T_QM_MAX, the detected user movement may be passed to the next steps of QM Identification.

When the concepts described in this example are extended to a system including one or more gyros, an additional requirement may be added to define a Pause. This requirement may be to ensure rotation no greater than a threshold A_ROT_MIN over the period of T_PAUSE_MIN. For example, the threshold A_ROT_MIN may be 10 degrees over the period of T_PAUSE_MIN. Since the output of a gyro is angular velocity with units of degrees per second (degrees/sec), the rotation over T_PAUSE_MIN may be calculated by integrating a gyro output over the period T_PAUSE_MIN. In addition, the start of a movement may be defined when the rotation over T_PAUSE_MIN exceeds A_ROT_MIN and end when the rotation decreases below A_ROT_MIN.

In summary, a Pause may be defined by a system with accelerometers and gyros simply as a period of T_PAUSE_MIN when the change in position and rotation of the wearable is less than the respective thresholds for position and rotation change over T_PAUSE_MIN. The Movement may begin roughly when either the change in position or rotation exceeds the respective thresholds for position and rotation change, and may end roughly when the next Pause is detected. The Pause may also be described as no movement or non-movement of the user and these terms can be used interchangeably. As discussed above, the pause, no movement or non-movement of the user can be a complete lack of movement or a negligible movement of the user. In some embodiments, the system can detect these slight movements but they may be identified as a Pause, no movement or non-movement of the user because the detected movement is below a movement threshold value and is therefore identified as a Pause.

Similar to the description of FIG. 2, the sensors used by the system to detect the pauses including the accelerometer and gyro may be 3-axis sensors and the resulting calculations may require computations in 3-D. The basic principles described in this application may be extended to 3-D using the appropriate mathematics. In the examples described with reference to FIG. 4 above, the Approximate Movement Duration, as opposed to an exact movement duration, is calculated by the system. While other methods may be utilized to calculate more precisely when the Movement begins and ends, an approximate value may be adequate for most applications of QM ID.

In an embodiment, the system's process for Qualifying Movement Identification (QM ID) may utilize Pauses to define boundaries at both the beginning and end of movements that may then be evaluated or tested to determine if these movements are QMs. Simple Identifiable Qualifying Movements (SIQMs) are made up of a number of basic QMs that are simple to identify for both a user and sensor algorithms. SIQMs may include basic movements such as user rotations. These SIQM rotations can include: a user axial rotation about a vertical Y axis in yaw, a user forward bending rotation about a horizontal X axis in pitch, a side bending rotation about a horizontal Z axis in roll or any combination of these rotational movements. Another example of basic movements that can be identified as SIQMs are user movements up to a standing or near standing position and movements down from the stand position or near the stand position. Other movements may be identified as SIQMs and identifiable using the disclosed, equivalent, or similar movement algorithms. In some embodiments, the SIQMs may be identified by the system as include more than one basic movement performed in sequence with one or more other basic movements. In other cases, more than one basic movement may be identified by the system as being part of the definition of a SIQM.

Rotation Thresholding may also be used to identify SIQMs that can include body rotations. In order to identify SIQMs that are not rotations such as up movements to a standing or near standing position and down movements from the standing or near standing position, two methods Trajectory Matching and Position Thresholding are proposed. These three approaches are described in more detail below.

An example of Rotation Thresholding is illustrated in FIGS. 5a-5d. FIG. 5a is a depiction of the front view of a user 101 at the start of a QM defining reference position P1 241 and FIG. 5b depicts a view of a user 101 after a rotation in the y-axis dimension at the end of the QM defining P2 242. FIG. 5c is top view of the same user 101 at P1 241 and FIG. 5d at P2 242. In FIGS. 5a-5d, the user 101 has rotated the body but the user's feet are stationary In Rotation Thresholding, the orientation of position P1 241 at the start of a movement is defined as the reference position and orientation of the wearable device. From the reference position and orientation P1 241 a user movement occurs and at the end of the movement, the rotation to position P2 242 is calculated relative to the orientation of P1 241 by the wearable device. If the rotation in a specific direction exceeds a threshold ROT_THRESH, then the movement may be considered to be a positive QM ID for that specific test by the wearable device.

System users can move with body rotation in various different directions as shown with reference to FIGS. 6a-6d illustrate user yaw rotation about a vertical Y axis, FIGS. 7a-7d illustrate user rolling rotation about a horizontal Z axis and FIGS. 8a-8d illustrate user pitch rotation about a horizontal X axis. Terms from Flight Dynamics including yaw, roll, and pitch are utilized in the following description. Rotations of the hips left or right may be considered yaw rotations and are shown in FIGS. 6a-6c. FIG. 6a illustrates a front view of a user 101 with the wearable device 290 in a straight standing position which can be the P1 position. FIG. 6b illustrates a user 101 in a yaw rotation to the left and FIG. 6c illustrates a user 101 in a yaw rotation to the right. FIG. 6d illustrates a top view an X-Z plane in a 3-Axis coordinate system where the top view is aligned with the Y-axis.

In FIG. 6d, an embodiment of yaw rotation thresholds is illustrated. The XZ plane yaw threshold angles are shown on FIG. 6d at the location of the wearable device 290 on the user 101 as shown in FIGS. 6a-6c. Note that in FIGS. 6a-6d, the Y-axis is shown upward and the Z-axis is denoted by the arrowhead coming out of the page. The XYZ axes are rotated 90 degrees such that the Y-axis is coming out of the page and the Z-axis is pointing downward. This is the equivalent of looking down from above the user. YAW_THRESH_L is the angle defining a threshold for a left rotation. For example, YAW_THRESH_L may be 45 degrees. If the sensors detect a yaw rotation left greater than 45 degrees, this detected rotation can result in a positive QM ID. Similarly, the YAW_THRESH_R is the angle defining a threshold for a right rotation and may also be 45 degrees. If the sensors detect a yaw rotation right greater than 45 degrees, this detected rotation can also result in a positive QM ID. Although YAW_THRESH_R and YAW_THRESH_L can be 45 degrees but in other embodiments these threshold angles can be any other value. In some embodiments, the threshold angles can be based upon the user's individual needs and can be asymmetric meaning that the YAW_THRESH_R and YAW_THRESH_L can be different values.

Similar parameters are presented for ROLL and PITCH rotations in FIGS. 7a-7d and FIGS. 8a-8d, respectively. With reference to FIG. 7a, a front view of a user 101 is illustrated in a standing position with the wearable device 290 oriented facing in the direction of the Z-axis in the XY plane. In FIG. 7b, a user 101 rotates in roll about the Z-axis to the right and FIG. 7c illustrates the user 101 rotating in roll about the Z-axis to the left. FIG. 7d illustrates an XYZ axis facing the Z-axis and XY plane. The ROLL_THRESH_R and ROLL_THRESH_L can be 45 degrees from the Y-axis about the Z-axis. In other embodiments, the ROLL_THRESH_R and ROLL_THRESH_L can be any other value. The threshold roll angles can be based upon the user's individual needs and can be asymmetric meaning that the ROLL_THRESH_R and ROLL_THRESH_L can be different values.

FIG. 8a illustrates a side view of a user 101 with the user 101 facing in the direction of the Z-axis. FIG. 8b illustrates the user 101 bending forward in pitch in the YZ plane about the X-axis. FIG. 8c illustrates the user 101 rotating back from a bent position to a straight arched position in pitch where the rotation is about the X-axis. FIG. 8d illustrates the threshold values for PITCH_THRESH_F and PITCH_THRESH_B. In the example, the forward rotation, PITCH_THRESH_F can be about 45 degrees while the PITCH_THRESH_B can be about 10 degrees.

In FIGS. 9a-9c and 10a-10g, similar threshold parameters are presented for seated rotations, in other words rotations while the user is seated. In FIG. 9a, a user 101 is depicted sitting deep back in a seat 151. This is the reference or P1 position as measured by the wearable device 290 which can define the XYZ axis orientations for measuring the threshold movements. In this example, the XYZ axis of the sensors is rotated about the X axis and the sensors are not in perfect vertical alignment with the Y axis which is angled backwards. In FIG. 9b, the user 101 is depicted in the P2 position where the user 101 has sat up and moved forward in the seat 151. This sitting up movement is a pitch rotation. Since the user 101 is seated, the movement is designated as an SPITCH rotation (with the letter S for seated preceding PITCH). SPITCH_F further designates that the pitch rotation is forward where _F designates forward. The rotation thresholds for SPITCH_F and SPITCH_B are shown FIG. 9c. As the user moves from P1 to P2, if the sensors in the wearable device detect a user 101 rotation in the SPITCH direction greater than SPITCH_THRESH_F, it will result in a positive QM ID by the system. It can be valuable to differentiate between a user 101 standing movement, sitting movement, and a laying down movement because it enables context dependent thresholds to be utilized for the same rotation. For example, a PITCH_THRESH_F may equal 22.5 degrees while SPITCH_THRESH_F may equal 45 degrees. These context dependent thresholds may be selected because the same pitch rotation of a user 101 while standing may put a higher degree of stress on the lumbosacral junction than while sitting due to differences in the way weight of the user's upper body may be supported in the two cases. Therefore, it may be desirable to protect a smaller pitch rotation while standing compared to when sitting.

In FIGS. 10a-10e, a seated yaw rotation left of a user 101 is illustrated. This rotation is similar to the movement of a user 101 moving into the right passenger seat of a vehicle. The side view shown of a user 101 seated in FIG. 10a can be prior to the rotation shown in FIG. 10c and FIG. 10e. The top view of the user 101 in the same seated position as FIG. 10a is shown in FIG. 10b where the XYZ axes are also shown. Since the user 101 rotation is a yaw rotation, it can be most convenient to view the user 101 from the top view.

In this example, P1 can be the user 101 seated facing in the Z-axis direction and P2 can be the user 101 after rotating to face the X-axis direction. While the final objective is a total of a 90 degree rotation relative to P1, a user may prefer to make this seated rotational movement in two steps with a roughly 45 degree rotation followed by a second 45 degree rotation. This two step movement can be depicted by a first 45 degree rotation shown in side view FIG. 10c and top view FIG. 10d. Following the first 45 degree rotation, the user 101 can perform a second step movement which can be an additional 45 degree rotation as shown in side view in FIG. 10e and in a top view in FIG. 10f. The threshold values for seated yaw are shown as SYAW_THRESH_L and SYAW_THRESH_R are shown in FIG. 10g.

The use and settings of the wearable device can change with body condition and experience. For example, a beginning user or one experiencing an episode of pain may prefer to make the shorter turn, whereas a more experienced user absent of pain may choose to make the 90 degree turn while bringing both feet into the vehicle during the same movement. The device may be programmed with data describing the user's experience level or their pain condition, and through look-up tables or similar means, the device may be setup with preferred settings for the specific conditions of a user. As the user becomes more experienced, heals and more flexible without pain, the system's threshold values can be changed to account for the improved mobility of the user. This demonstrates the flexibility of the device settings and customization of the inventive system to be configured, optimized, and customized for the personalized physical condition of each user.

The wearable device can also detect user 101 movements in other situations. For example, FIGS. 11a-11g illustrates movements and rotations associated with a user transitioning from 101 laying down to getting up out of bed 181. With reference to FIG. 11a, a user 101 is illustrated laying down in the reference P1 position. The XYZ coordinate system is associated with the position of the wearable device 290. The Y-axis is aligned with the height of the user 101 and the length of the bed 181. The X-axis is aligned with the width of the user 101 and across the width of the bed 181 and the Z-axis is aligned upward out of the user 101 and bed 181. With reference to FIG. 11b, when the user 101 gets up from a back sleeping laying down position, the user 101 may rotate with the wearable device 290 to the left in a yaw rotation about the Y-axis. The P2 position after a 90 degree yaw rotation is shown in FIG. 1' 1b. The rotation thresholds are shown in FIG. 11f and defined by LYAW_THRESH_L and LYAW_THRESH_R where "L" indicates laying down. In this example, the LYAW_THRESH_L and LYAW_THRESH_R can each be 45 degrees and the 90 degree user rotation from P1 to P2 can exceed the LYAW_THRESH_R which can indicate a QM.

Once this P1 to P2 QM has been completed and the user pauses, the wearable device 290 may detect this pause to complete the QM and the wearable device 290 can then be ready to detect a subsequent user 101 movement. For example, after the wearable device 290 detects a pause finishing the QM, the position of FIG. 11b becomes the P1 position for the next movement as shown in FIG. 11c. The wearable device 290 can detect that a rolling rotation of the user 101 has been initiated and during the roll rotation, the wearable device 290 may encourage the users 101 to use their hands to push themselves up to aid in the movement upright as shown in FIG. 11d through an output device. The P2 position after a full 90 degree ROLL rotation about the Z-axis to the right is shown in FIG. 11e. Thresholds for the LROLL_THRESH_R AND LROLL_THRESH_L rotations are shown in FIG. 11g and in this example, the threshold values can be 45 degrees. The user's right roll rotation about the Z-axis from P1 (FIG. 11c) to P2 (FIG. 11e) exceed 45 degrees which can interpreted as a QM. Again, the user 101 may pause at the edge of the bed 180 prior to their next movement as shown in FIG. 11e. The wearable device 290 can detect the pause at the end of the QM and prepare to detect the next subsequent user 101 movement.

In different embodiments, the system can identify QMs as protected QMs based upon the core contraction timing. In a first embodiment, the system can be configured to analyze each distinct movement and identify a protected QM when the core contraction begins during the pause before the movement and through the movement to the pause at the end of the movement. In a second embodiment, a movement may be identified as a protected QM by the system when the core contraction occurs during the movement. In a third embodiment, a movement may be identified as a protected QM by the system when the core contraction occurs during most of the movement.

In an embodiment, the wearable device can perform a Trajectory Matching process for identifying a sequence of positions in 3-D space of the wearable device that define a specific movement. With reference to FIG. 12a, the trajectory of the wearable device 290 worn on a user 101 standing up from a sitting position is shown. With reference to FIG. 12b, the trajectory of the wearable device 290 from P1 241 to P1 242 is shown in isolation. In general, the positions may be many points in 3-D space however the trajectory position points are shown in FIGS. 12b-12c in a two dimensional vertical plane for simplicity. The sequence begins around the time movement of the wearable device 290 is detected, and may end when a pause is detected after the end of the movement. In FIG. 12c, a target trajectory for a particular movement is defined, starting from P1 241 and ending at P2 242. The samples shown as filled circles are defined at a pre-defined sample rate with the same time period between adjacent circles. Therefore, the relative speed of the wearable device 290 moving from P1 241 to P2 242 may be captured by the target trajectory.

The target trajectory can then be scaled in both time and position to match the actual trajectory of the wearable device 290 at the end points P1 241 and P2 242 as shown in FIG. 12d. The time element may also be captured by using interpolation to resample the actual trajectory 183 samples A1-A6 to be at a similar rate as the target trajectory 185 samples T1-T6. Alternatively, samples of the target trajectory 185 may be resampled using interpolation to obtain samples in a similar time scale as the actual trajectory 183 samples. These computations allow a Euclidean Metric to be calculated between the actual trajectory 183 and the target trajectory 185 as shown in FIG. 9d. The equation for Euclidean Metric is below where $T_k$ and $A_k$ are the Target Trajectory and Actual Trajectory sample points respectively at time k.

$$\text{Euclidean Metric} = \sum_{k=1}^{6} (T_k - A_k)^2$$

If more than one Target Trajectory corresponding to different Qualifying Movements is defined, the one with the smallest Euclidean Metric can be the Maximum Likelihood solution among the tested Target Trajectories. A practical implementation may require that the smallest Euclidean Metric is less than a minimum threshold to ensure that the most likely solution is also a good solution. In other words, a metric may be used to ensure that the Actual Trajectory is somewhat close to the most likely Target Trajectory. The use of 6 samples in the Euclidean Metric equation above is arbitrary for purposes of the illustration. Any number of samples greater than one may be used in the calculation.

The Trajectory Matching by the wearable device may allow subtle movements to be tracked and enable a maximum likelihood selection of a QM. However, for the objective of QM ID, Trajectory Matching may be cumbersome since it may be extremely computationally intensive. Arbitrary scaling and resampling in 3-D, while being algorithmically simple, can require a high degree of processing power. Furthermore, specific trajectories must be followed by the user for effective QM ID.

A more computationally efficient approach for QM ID can be Position Thresholding which can be performed by elements of the wearable device. Examples of Position Thresholding are illustrated in FIGS. 13a-13c and 14a-14d. In Position Thresholding, elements of the wearable device can define the position P1 241 at the start of a movement as the reference point or reference position and orientation. The wearable device can then detect the end of the movement, position P2 242 and calculate the movement to position and orientation P2 242 relative to the position and orientation of P1 241.

In an embodiment, the Threshold Box 187 may be as shown in FIG. 13c. Movement of the wearable device 290 from P1 241 to P2 242 may be broken into Y-dimension Movement 95 and Z-dimension Movement 97. If Y-dimension Movement 95 is greater than Y-dimension Threshold 93 and Z-dimension Movement 97 is greater than Z-dimension Threshold 95, P1 242 has moved into the Threshold Box 187 and this movement analyzed by the system is identified as a Qualifying Movement.

Figure 14A:
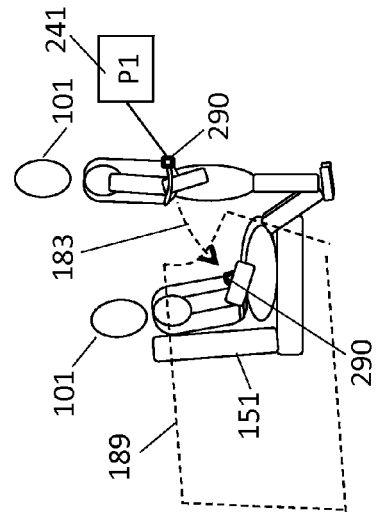
FIG. 14a illustrates an embodiment of a sit-to-stand Threshold Box for Position Thresholding.

A 3-D volume we refer to as the Threshold Box may be defined for each QM. An example of a Threshold Box 187 is shown in FIG. 14a. The Threshold Box 187 may be referenced to the position and orientation of P1 241. Details of the Threshold Box 187 may depend on physical characteristics of the user 101 such as height, shoulder width, and in-seem. The Threshold Box 187 defines a threshold for each QM such that if the Threshold Box 187 touches or contains P2 242, it is considered a positive QM ID for that specific test performed by the system. Because the user must move device 290 into the Threshold Box 187 at P2 242, the P1 241 position may not be located within the Threshold Box 187.

Figure 14B:
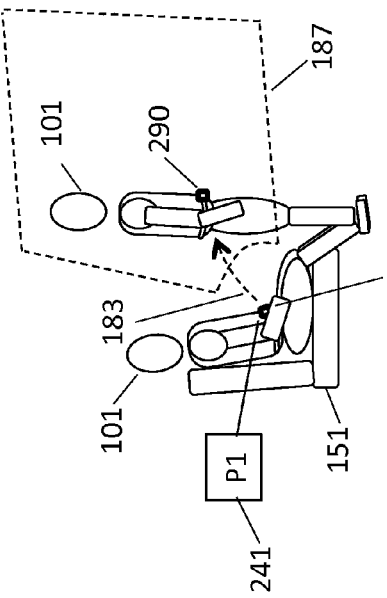
FIG. 14b illustrates an embodiment of a stand-to-sit Threshold Box for Position Thresholding.
Figure 15B:
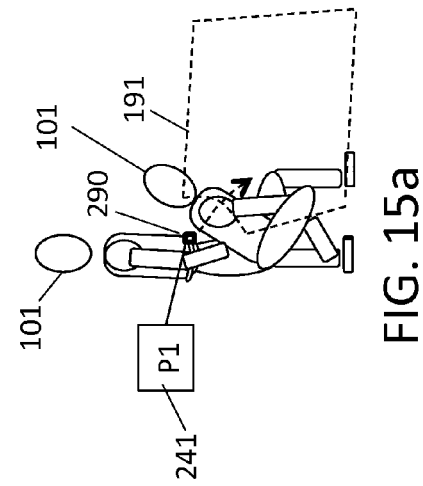
FIG. 15b illustrates an embodiment of a crouch-to-stand Threshold Box for Position Thresholding.

Another Threshold Box 189 is shown in FIG. 14b to further illustrate an example of the Threshold Box 189. One of the metrics defining the Threshold Boxes 187, 189 may be the minimum distance between P1 242 and P2 241. This may define a sphere around P1 241 or more specifically a sphere around the wearable device in P1 241 that then defines a spherical surface of the 3-D Threshold Boxes 187, 189 nearest to P1 241. In this Sit-to-Stand example shown in FIG. 14a, the width of the Threshold Box 187 can be roughly the shoulder width of the user 101. Furthermore, the Threshold Box 187 is forward and up relative to P1 241 as shown by the angles of the Threshold Box 187 on the side of the user 101. Note that the vertical face of the Threshold Box 187 nearest the user moves away from the user 101 as the distance from P1 241 increases, and the horizontal face on the bottom of the Threshold Box 187 moves away from the ground as the distance from P1 241 increases. While the Threshold Box 187 is shown to be truncated on the sides of the box away from the user 101, it may extend arbitrarily far from the user though doing so may be of limited or negligible value.

Figure 15A:
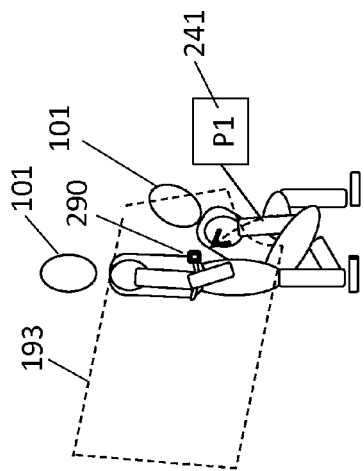
FIG. 15a illustrates an embodiment of a stand-to-crouch Threshold Box for Position Thresholding.

In FIGS. 14a, 14b, 15a and 15b, examples of Threshold Boxes are shown for examples of SIQMs. In FIG. 14a, the sit-to-stand Threshold Box 187 is shown as has been previously described. In FIG. 14b, the stand-to-sit Threshold Box 189 is shown. Note that as defined, this may expect a backward and downward movement. The crouching movement of FIGS. 15a and 15b may be used when picking something off of the floor or placing something onto the floor. In FIG. 15a, the stand-to-crouch Threshold Box 191 is shown. This differs from the stand-to-sit Threshold Box 189 shown in FIG. 14b because the system is expecting a forward and downward movement to a crouched position shown in FIG. 15a as opposed to the backward and downward movement expected by the stand-to-sit Threshold Box 189 shown in FIG. 14b. In FIG. 14b, the crouch-to-stand Threshold Box is shown. As defined, this may expect a backward and upward movement.

The system may anticipate or predict a next movement of a user 101 based upon the current state of the user 101 and the current state of the user 101 may be based upon the last detected movement of the wearable device 290. For example, if the last detected position of the user 101 is in a seated position, the next expected movement predicted by the wearable device 290 can be a movement to a standing position as shown in FIG. 14a. If the last detected position is a standing position and the system detects a backward down movement, the system can predict that the next movement can be to a seated position as shown in FIG. 14b. If the last detected position is a standing position and the system detects a forward down movement, the system can predict that the next movement can be to a crouched position as shown in FIG. 14c. If the last detected position is a lowered crouched position, the system can predict the next movement to be to a standing position.

Position Thresholding has several attractive attributes. First, specific user trajectories do not need to be followed by the wearable device. The wearable device may only need to detect position and orientation changes from P1 to P2 in the evaluation of a movement as a QM in some embodiments of the invention and intermediate user positions between P1 and P2 do not need to be determined. Second, when only changes in position and orientation from P1 to P2 are evaluated for the duration of a QM or less, the effect of integrating and double integrating offsets may be neglected since the impact of these offsets may be small due to the limited integration intervals. Third, the model may be refined and optimized for a particular user with data describing physical characteristics of the user. And fourth, the thresholds may be modified depending on the condition of the user.

The user's state at the start of a movement (P1) may be used, in part, to identify a QM or modify thresholds for QM ID by the wearable device system. Examples of user states that can be useful in determining the QM ID by the wearable device system include: Standing or Stand, where the user is standing up; Sitting or Sit, where the user is seated; Laying Down, where the user is laying for example on a bed or a sofa; and Riding Transportation. Other user states may be utilized in different applications. In some applications, it may be beneficial to further qualify or further define user states as Application States by the wearable device system. For example, riding the bus while standing may be an application state as it defines with greater detail the user's state. While a user's state may be detected or detectable through algorithms used by the wearable device system, some Application States may be set or selected through software running on the wearable system, a handheld device or app which may be part of the wearable system and configured to modify some parameters in QM ID. Some Application States may also define new QMs that may be applied only during certain Application States.

User state information may be used to qualify thresholds. For example, a rotation to the left when a user is standing may be configured to use a QM ID rotation threshold of 45 degrees, while the threshold that may be used when a user is seated may be set to 22.5 degrees since the body movements involved in rotating during sitting may result in greater stress to the lumbosacral junction than the stress in rotating while standing. As a result, a smaller thresholds may be used while sitting compared with the thresholds used for rotating while standing. This assignment of thresholds may be reversed for some users. Furthermore, the detected user states may provide context to interpret and further identify movements. For example, if a user is riding in a transportation vehicle, then the algorithms may have provisions to take this into account. The acceleration experienced in a vehicle is generally quite different than the acceleration experienced standing up from a sitting position. However, if the system algorithms are able to identify that the user is riding in a vehicle, they may be able to ignore what may be false positive QM IDs due to movement of the vehicle. If a user is standing while riding a bus, support of the core while starting and stopping may be beneficial. This is an example of how refinements in Application States is possible and potentially beneficial to the usefulness of the inventive system.

The system can be used in two examples that further illustrate this inventive approach to QM ID. Users can be encouraged through an output of the system to execute basic everyday movements in a deliberate manner, breaking movements down into controlled basic movements or SIQMs. This facilitates utilizing core contractions to protect the lumbosacral junction and lumbar spine during QMs. Rotation Thresholding is a subset of Position Thresholding where only changes in rotation from P1 to P2 are evaluated. Position Thresholding and Rotation Thresholding can also be used in the QM ID procedures in the following examples.

Various methods have been disclosed for identifying QMs. In a first method, the system can identify QMs by identifying a non-movement (NM) (no movement, pause etc.), identifying a start of a movement and a subsequent NM. The system can then determine the duration of the detected movement between the starting and ending NMs. If the detected movement meets the time duration requirements, the movement can be identified as a potential QM and a QM ID (or QMID) can be performed on the sensor data associated with the movement.

In a second method, the system can identify a NM and then identify the start of a movement. The system can then perform QM ID on the sensor data for a duration of time to identify the movement as a QM. The duration of time required for a QM may depend on several factors including the pain condition and fitness level of the user, as well as the QM being tested.

In a third method, the system can identify an NM and then perform QM ID from the next sample until the next NM is detected. If a QM is identified before the second NM is detected, the system can review the recorded data to determine the start of the movement. The duration of time from the determined start of the movement to the second NM can determine the duration of the QM. This approach may be less attractive since the time between starting and ending NMs may be arbitrarily long, resulting in sensor offsets being integrated and double integrated requiring DC offset or auto-zeroing techniques to be included in the algorithms as discussed earlier.

In a fourth method, the system can identify a NM and evaluate from a next sensor sample interval for a first duration of time to identify a QM. This process can be repeated with the system evaluating the start of a second sensor sample interval for a second duration of time, evaluating a start of a third sensor sample interval for a third duration of time, etc. The first, second, third, and subsequent durations of time may be the same in value, and similar to the duration of time described in the second method. Evaluation for QM ID for a duration of time effectively defines an evaluation window. In this fourth method, QM ID evaluation occurs in parallel evaluation windows, delayed by one sensor sample interval. This process is performed until a QM ID is positive. The first and second methods can be more computationally efficient than the third and fourth methods and this can improve system performance. In other embodiments, other methods can be used to determine QMs.

Figure 16:
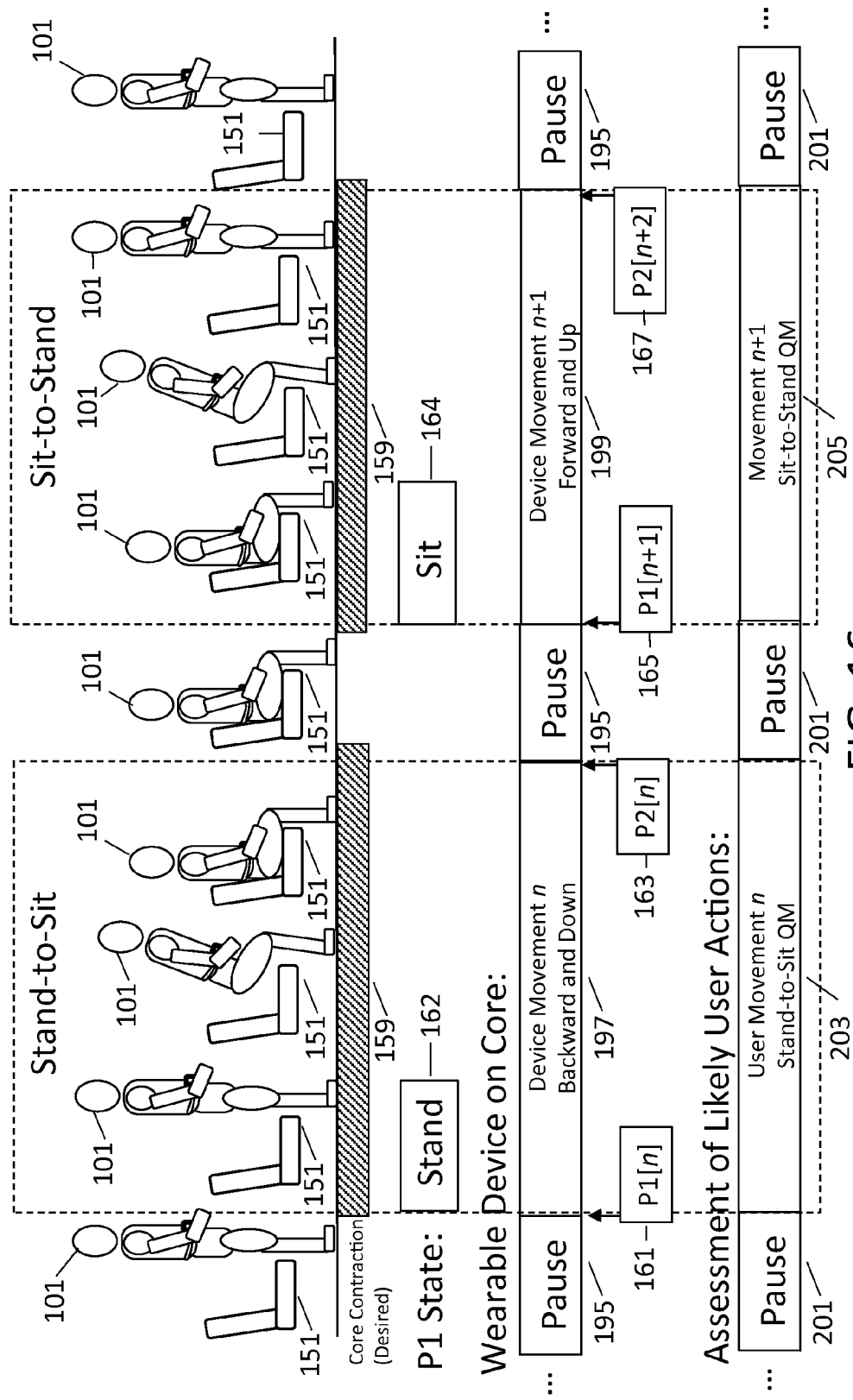
FIG. 16 illustrates an embodiment of a user moving from standing to sitting to standing position with pauses between movements with data from the wearable device worn by the user and the assessments of the likely actions of the user identified by the processor based on the data from the wearable device and the user's state at P1.

Examples of the processes for analyzing the detected movements and core contractions during movements are illustrated with reference to FIGS. 16 and 17. In a first example illustrated in FIG. 16, a user 101 begins in the stand position, moves to the sit position on a chair 151, pauses, then moves back from the sit position to the stand position in a left to right sequence. The user's 101 position at P1[n] 161 is shown on the left and the user's 101 position at P2[n] 163 is shown on the right of the stand-to-sit movement 381. The user's 101 position at P1[n+1] 165 is shown on the left and the user's 101 position at P2[n+1] 167 is shown on the right of the sit-to-stand movement 383. Note the pauses 385 at the start, between the stand-to-sit movement 381 and the sit-to-stand movement 383, and finally at the end. Breaking the movements into steps such as demonstrated in this example encourages users 101 to deliberately and carefully execute the movements. The wearable device 290 is shown on the user 101 and the Threshold Box for the stand-to-sit QM 189 is shown relative to the position and orientation of the wearable 290 at P1[n] in the left of stand-to-sit movement 381. The wearable device 290 is shown on the user 101 and the Threshold Box for the sit-to-stand QM 187 is shown relative to the position and orientation of the wearable 290 at P1[n+1] in the left of sit-to-stand movement 383. Signals from the movement sensors in the wearable device 290 are transmitted to a processor which interprets the data from the movement sensors. Based on the detected user movements utilizing the sensor data, the system algorithms must assess whether or not the user movement should be identified as a QM.

The system can first assess Movement n. Utilizing Position Thresholding, the change in a user's position and orientation from P1[n] to P2[n] is a movement backwards and downwards. For illustration purposes, the movement backwards and downwards can be measured to be 12 inches and 10 inches, respectively. Further assume this places P2 in the Threshold Box for a stand-to-sit QM 189. The system's assessment would be that the user 101 performed a stand-to-sit movement and a QM is positively identified. The system would then determine if the user's core was appropriately contracted before, during, and just after the duration of the QM movement, and signal appropriately to the user through an output device which can produce an audio, visual or any other type signal. In this example, the core contraction sensor can detect the core contractions 159 before the start, during and after the end of the standing to sitting movement 381.

Next, the system can assess Movement n+1. The change in position and orientation from P1 to P2 can be detected by the movement sensors in the wearable device as a movement forward 12 inches and upward 10 inches. Again, utilizing Position Thresholding, P2 is identified to be in the Threshold Box for a sit-to-stand QM 187. The assessment would be that the user performed a sit-to-stand movement and a QM is positively identified. The system would then again determine if the user's core was appropriately contracted before, during, and just after the duration of the QM, and signal appropriately to the user. Since specific QMs are identified, the specific relationships of the timing of the core contractions 159 to the movements may be assessed, taking into account the condition and fitness level of the user 101. Since the QM ID blocks operate effectively in parallel in the assessment of a QM, we need not additionally assess rotations when QMs were already identified by the approaches taken in the description.

Figure 17:
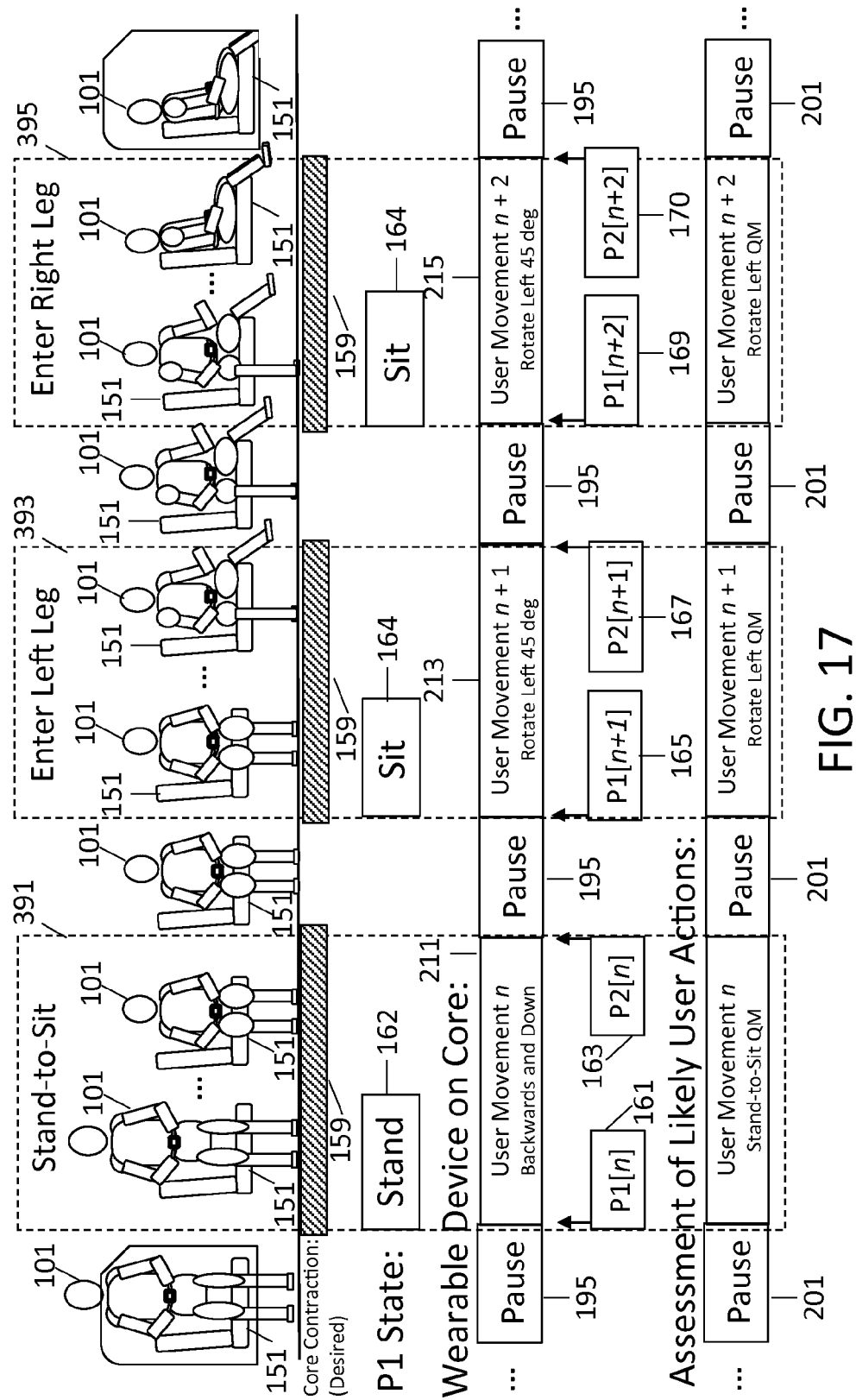
FIG. 17 illustrates an embodiment of a user moving from the stand position to entering a vehicle on the passenger side with pauses between movements with data from the wearable device worn by the user and the assessments of the likely actions of the user identified by the processor based on the data from the wearable device and the user's state at P1.

In the second example with reference to FIG. 17, a user 101 is depicted as standing, then going into the passenger side seat 159 of a vehicle in a sequence of pictures from left to right. The user 101 begins in the position of stand, moving to the position of Sit 391, pausing 195, then rotating approximately 45 degrees to the left as the user's left foot is placed into the vehicle, pausing 195, then rotating another approximately 45 degrees to the left as the user's right foot is also placed into the vehicle as shown in FIG. 14a. Note the pauses 195 at the start, between sitting down and rotating left 393, then again before rotating left again 395, and finally at the end. Threshold Boxes are not shown in this example.

The system can estimate the user's P1 state as shown in FIG. 17. The P1 state may be utilized to choose thresholds for the QM ID algorithm. The movement sensors in the wearable device 290 can transmit movement signals to a processor that can indicate an initial pause 195, a Movement n 211 between P1[n] 161 and P2[n] 163 and the following pause 195 in response to the stand-to-sit movement 391. The movement sensors can then transmit movement signals indicating: a pause 195, a first 45 degree rotation 213 between P1[n+1] 165 and P2[n+1] 167 and a pause 195 in response to a first rotating left 45 degree movement 393. The movement sensors can emit movement signals that indicate a pause 195, a second 45 degree rotation between P1[n+2] 169 and P2[n+2] 170 and a pause 195 in response to a second rotating left 45 degree movement 395.

Signals from the movement sensors in the wearable device 290 and interpretations of data from the sensors can indicate the likely user actions and the likely user actions can be based on the user's state and the detected movements based on the sensor data. The algorithms can assess whether or not each movement should be identified as a QM.

Referring to FIG. 17, the processor can first assess Movement n. Based on prior movements, the algorithms may assess that the user's state is Stand. Utilizing Position Thresholding, the change in position and orientation from P1 to P2 is a movement backwards and downwards. For illustration purposes, the system may detect the movement backwards and downwards are measured to be 12 inches and 10 inches, respectively. Further assume this places P2 in the Threshold Box for a stand-to-sit movement. Based upon the sensor data and movement algorithm processing, the system processor assessment would be that the user 101 performed a pause 201, a stand-to-sit QM 391 and another pause 201.

The system would then determine if the user's core was appropriately contracted before, during, and just after the duration of the stand-to-sit QM 391, and signal appropriately to the user. This would also confirm the user state was likely stand at P1[n] 161. Signals transmitted from the core sensor to the processor can indicate that the core was contracted before, during, and just after the duration of the stand-to-sit QM 391. Thus, the system can determine that the stand-to-sit QM 391 is a protected movement.

Next, the system can assess Movement n+1. Since a stand-to-sit movement 391 was assessed previously, the user's state is assessed to be Sit at P1[n+1]. The change in position and orientation from P1[n+1] to P2[n+1] can be detected by the movement sensors is a rotation left (YAW rotation) of 45 degrees. Rotation Thresholding may be utilized by the processor for this left rotation. Since the user's state was assessed to be Sit, the SYAW_THRESH_L is the threshold to test against, as opposed to YAW_THRESH_L which would be used if the user state was assessed as standing. Suppose SYAW_THRESH_L=22.5 degrees. Then, since the measured rotation is 45 degrees and greater than 22.5 degrees, the system can identify a positive QM ID.

Finally, the system can assess Movement n+2. The user's state is assessed to still be Sit at P1[n+2]. The change in position and orientation from P1[n+2] to P2[n+2] detected by the movement sensors is a rotation further left (YAW rotation) of 45 degrees for the user to get the user's right leg into the vehicle. Rotation Thresholding may again be utilized to assess this left rotation. Since the user's state was assessed to be Sit, the SYAW_THRESH_L is the threshold to test against. Using SYAW_THRESH_L=22.5 degrees, since the measured second rotation is 45 degrees which is greater than 22.5 degrees, the system can detect another positive QM ID. The system assessment would be that the user 101 performed a 45 degree YAW left rotation and a QM is positively identified. The system would then again determine if the user's core contraction 159 was performed before, during, and just after the duration of the QM, and the system can emit a signal appropriately to the user 101. Since specific QMs are identified, the specific relationships of the timing of the core contractions 159 to the movements may be assessed, taking into account the condition and fitness level of the user 101.

An important aspect of the present invention is that the parameters of the algorithms for QM ID can be determined using different conditions and criteria which can include the user's pain condition, physical characteristics, skill in timing the user of the core muscles and other criteria. These parameters may be changed as the user's condition, physical characteristics and skill in timing the use of core muscles changes. As described above, the duration of the QM ID is variable and may be set by criteria that includes a typical time duration for the user to perform a specific QM. If a user experiences an episode of back pain, the user is likely to respond to this pain by moving more slowly than prior to the pain. The QM evaluation duration may be made longer for a person experiencing back pain than a user who is not in pain.

When a system user experiences an episode of back pain, in addition to moving more slowly, the user may benefit from contracting the core muscles during smaller magnitude movements. For example, if a user is healthy and standing, the user may be comfortable and experience little benefit from contracting the core for a vertical axis rotation to the left of 30 degrees or more. However, if the user is experiencing an episode of back pain, the user may find a benefit in supporting the lumbosacral junction during rotational turns as little as 15 degrees or less. In these examples, a healthy user may have a threshold for rotation of about 45 degrees when the back is healthy but this threshold may be reduced to about 15 degrees when the user is experiencing episodes of back pain.

In different embodiments, various methods can be used to perform the calibration of the sensors and device so that the threshold values are accurately determined for the user. In an embodiment, the user can perform specific movements and based upon the sensor data, the system can determine threshold parameters. For example, the user can repeat sit-to-stand and stand-to-sit movements 10 times. The system can record these movements and determine average P1 to P2 locations that define the movements for the user based upon these recorded values. In an embodiment, the system communications unit 331 shown in FIG. 1*c* can communicate to a computer, handheld device, smart device or other which may provide a user interface for example, in the form of an app, that can provide calibration instructions to the user and input the settings based from the calibration process. In some cases, the system can be configured with settings based upon the physical characteristics of the user such as height, weight, etc. A small movement may be identified as a QM for a shorter user, while this same small movement may not be identified as a QM for a taller user. Similarly, a small movement may be identified as a QM for an injured user, while this same small movement may not be identified as a QM for a healthy user. Because users are in a wide variety of sizes and conditions, the system must be adaptable for every possible user.

In other embodiments, the user may be able to self define the setting and threshold values and input this information to the system through, for example on an app running on a smart device to the system communications unit 331 shown in FIG. 1*c*. The user may determine that the settings and/or threshold values need to be adjusted and in an embodiment, user adjustments can be made.

Figure 18A:
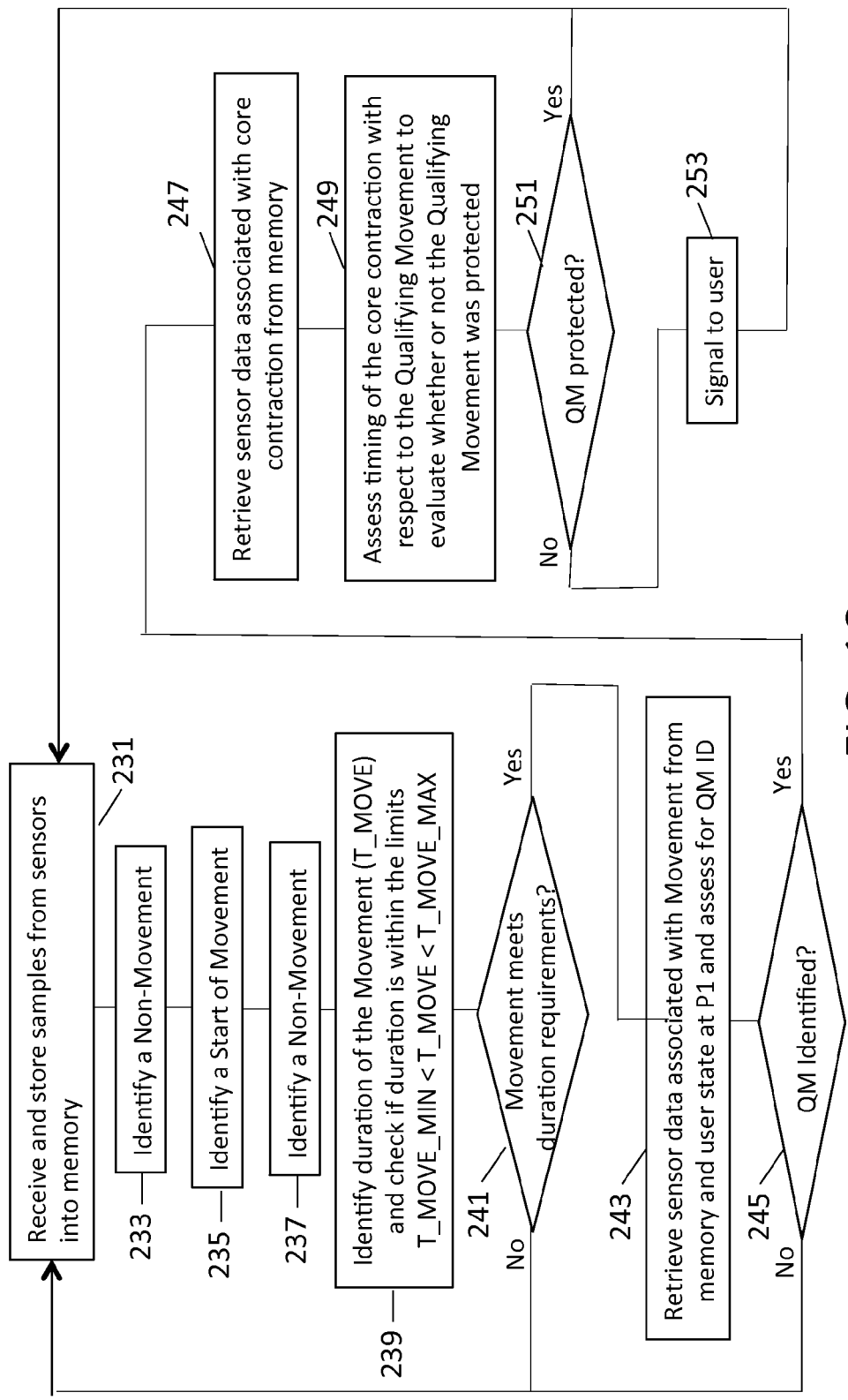
FIGS. 18a and 18b illustrate flow diagrams starting with receiving data from sensors, through assessing QM ID, through comparing the user's core contraction with the timing of the QM, and providing feedback to the user.

A basic flow diagram for testing movements as QMs is shown in FIG. 18*a*. Samples from the sensors are stored in memory 231. In the first phase, the system can identify a user movement by first identifying a non-movement (pause) 233. The system can then identify a start of a movement 235 when user movement is detected. The system can identify the end of the movement by detecting a second non-movement (pause) 237. The system can then check if the time duration of the Movement, with a non-movement (pause) 237 both before and after, qualifies it as a potential QM 239. If the Movement is too short or too long, the system can return to identifying the next sequence of non-movement 233, start of movement 235 and non-movement 233. When a Movement meets the time requirement to be a QM, retrieve the estimate of the state at P1 and perform QM ID tests utilizing the sensor data 243. If one or more of the QM ID tests is positive, a QM is identified 245. If the Movement is not a QM, the system can return to identifying the next sequence of non-movement 233, start of movement 235 and non-movement 233. In an embodiment, the user state at P1 may not be used and context dependent thresholds may not be used.

If the movement is a QM, the system can retrieve sensor data corresponding to contraction of the user's core 247. The time period for the sensor data can depend upon the configuration of the system and the desired contraction can vary depending upon the system configuration. In an embodiment, the required core contraction can extend into the periods of the Pauses before and after the Movement. In other embodiments, the system may be configured to only require core contraction during a portion of the movement. The system can compare the core contraction to the timing of the Movement. In a conservative test for a protected movement, the core should be contracted before the Movement begins and should stay contracted until after the Movement ends 249. If the core is properly contracted over the appropriate period of time, the QM is considered protected 251. Generally, the device or system may signal to the user when the Movement is not protected 253. In some applications, the system may also signal to the user when the Movement is properly protected. In either case, at the end of this process, return to evaluating samples 231, and repeating the described process again.

Figure 18B:
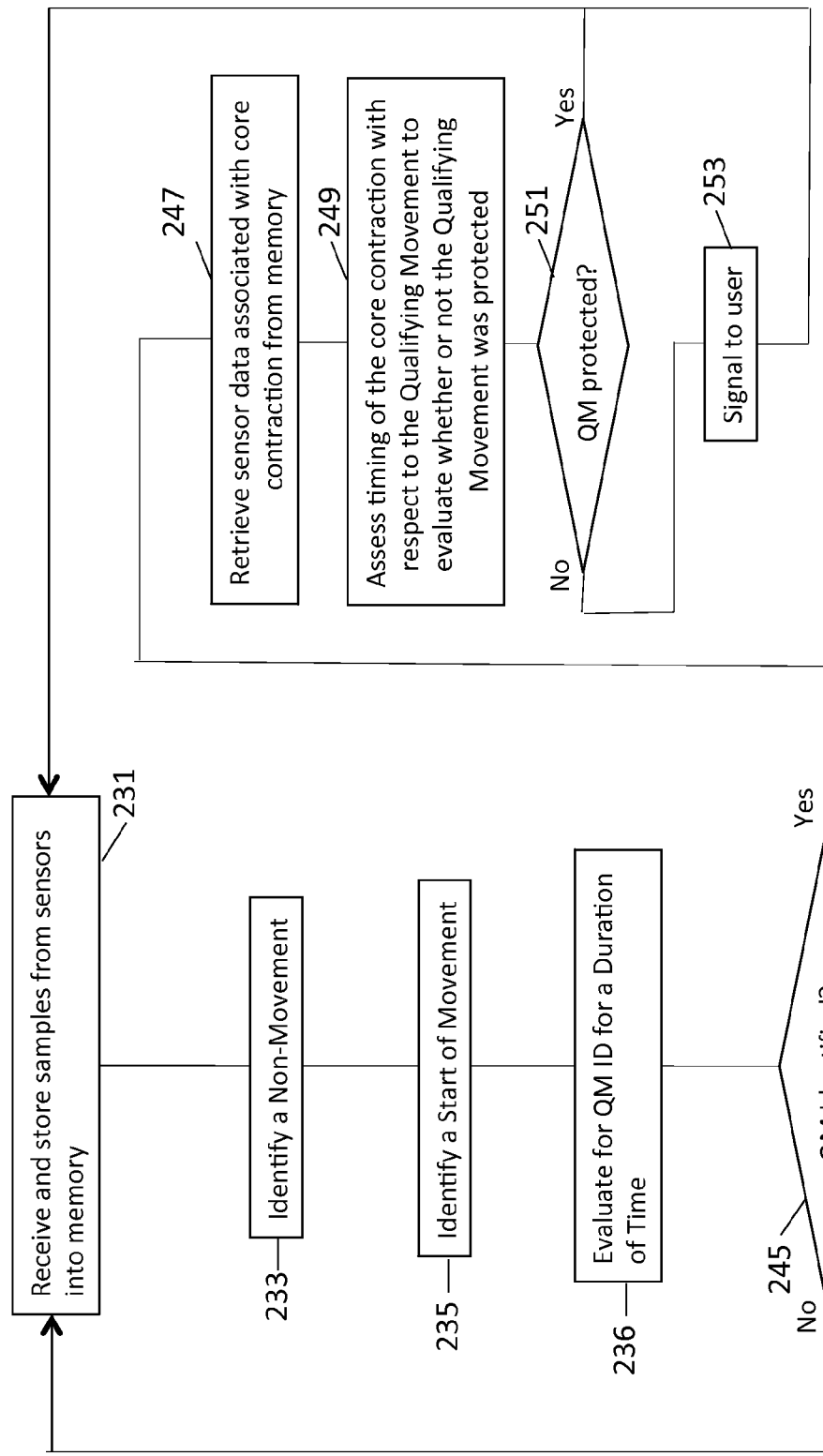

Another flow diagram for testing movements as QMs is shown in FIG. 18*b*. Samples from the sensors are stored in memory 231. In the first phase, the system can identify a user movement by first identifying a non-movement (pause) 233 and then identify a start of a movement 235. The system can then evaluate sensor data for QM ID for a duration of time 236. If one or more of the QM ID tests is positive, a QM is identified 245. If the Movement is not a QM, the system can return to identifying the next sequence of non-movement 233, start of movement 235 and QM ID for a duration of time 236.

If the movement is a QM, the system can retrieve sensor data corresponding to contraction of the user's core during the time period starting before the Movement began until after the QM ID duration of time from memory 247. The system can compare the core contraction to the timing of the Movement to evaluate whether the movement is a qualifying movement that is protected 249. If the core is properly contracted over the appropriate period of time, the QM is considered protected 251. The device or system may signal the user when the Movement is not protected 253. At the end of the illustrated process, the system returns to evaluating user activity samples and identifying pauses and movements, and repeat this process again.

Figure 19:
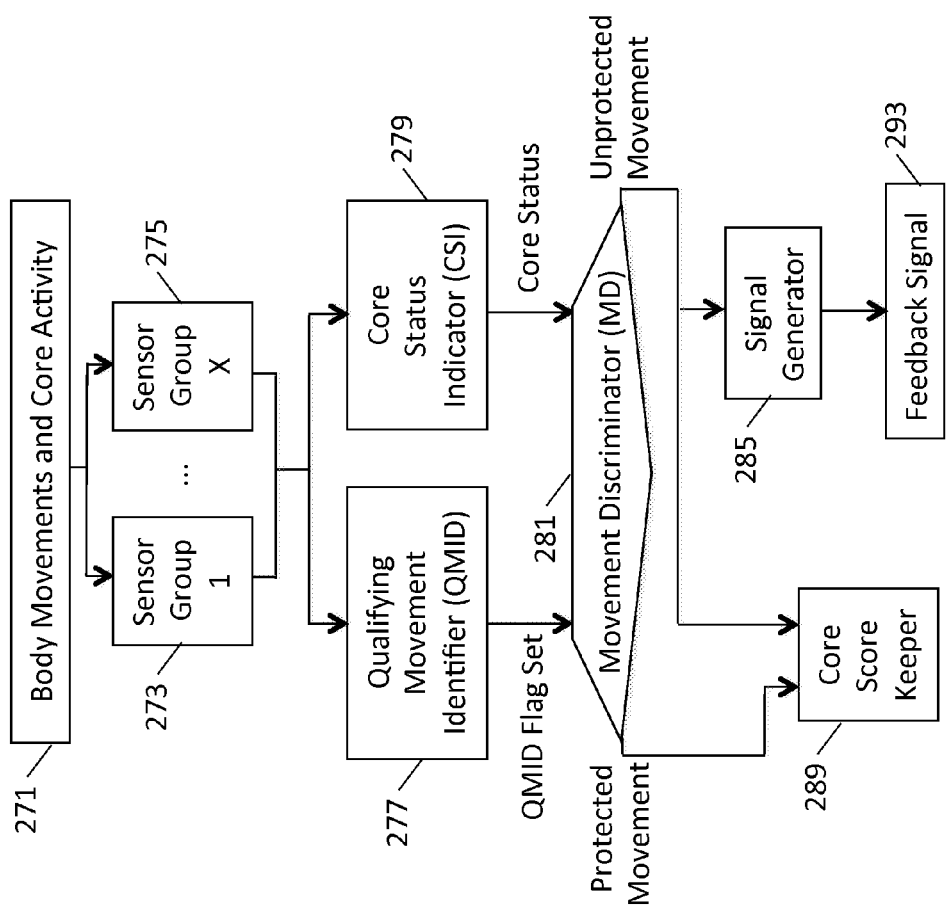
FIG. 19 illustrate flow diagrams starting with receiving data from sensors, through assessing QM ID, through comparing the user's core contraction with the timing of the QM, providing feedback to the user and recording protected and unprotected QMs.

In U.S. patent application Ser. No. 14/132,808, an example of the signal processing blocks in a preferred embodiment is shown (see FIG. 33*a* of U.S. patent application Ser. No. 14/132,808). A similar configuration of signal processing blocks is illustrated in FIG. 19. The user body movement and core activities 271 can be detected by a sensor group 1 273, other sensor groups and sensor group X 275. The sensor groups 273, 275 can send user movement signals and core contraction signals to the qualifying movement identifier QMID 277 and core status indicator (CSI) 279. The qualifying movement identifier QMID 277 and the core status indicator (CSI) 279 can be algorithms running on a processor. The QMID 277 can transmit a QMID Flag Set data and the CSI 279 can transmit core status information to a movement discriminator (MD) 281 which can determine if the QMs are protected or unprotected. The processor may transmit both the protected qualifying movement and unprotected qualifying movement decisions to a Core Score keeper 289 which can record and store the user data. The user can determine a Core Score by determining a percentage of times that the QMs were protected compared to unprotected. In an embodiment, a user will have a higher core score when the user has a higher percentage of protected QMs than non-protected QMs. Unprotected movement signals can be transmitted to a signal generator 285 which can provide a negative feedback signal to a user when an unprotected QM is detected by the system. The feedback signal can provide an incentive for the user to perform protected QMs rather than unprotected QMs. The feedback can be an audio, visual or any other output that will be easily identified by the user as an unprotected QM signal.

Figure 20:
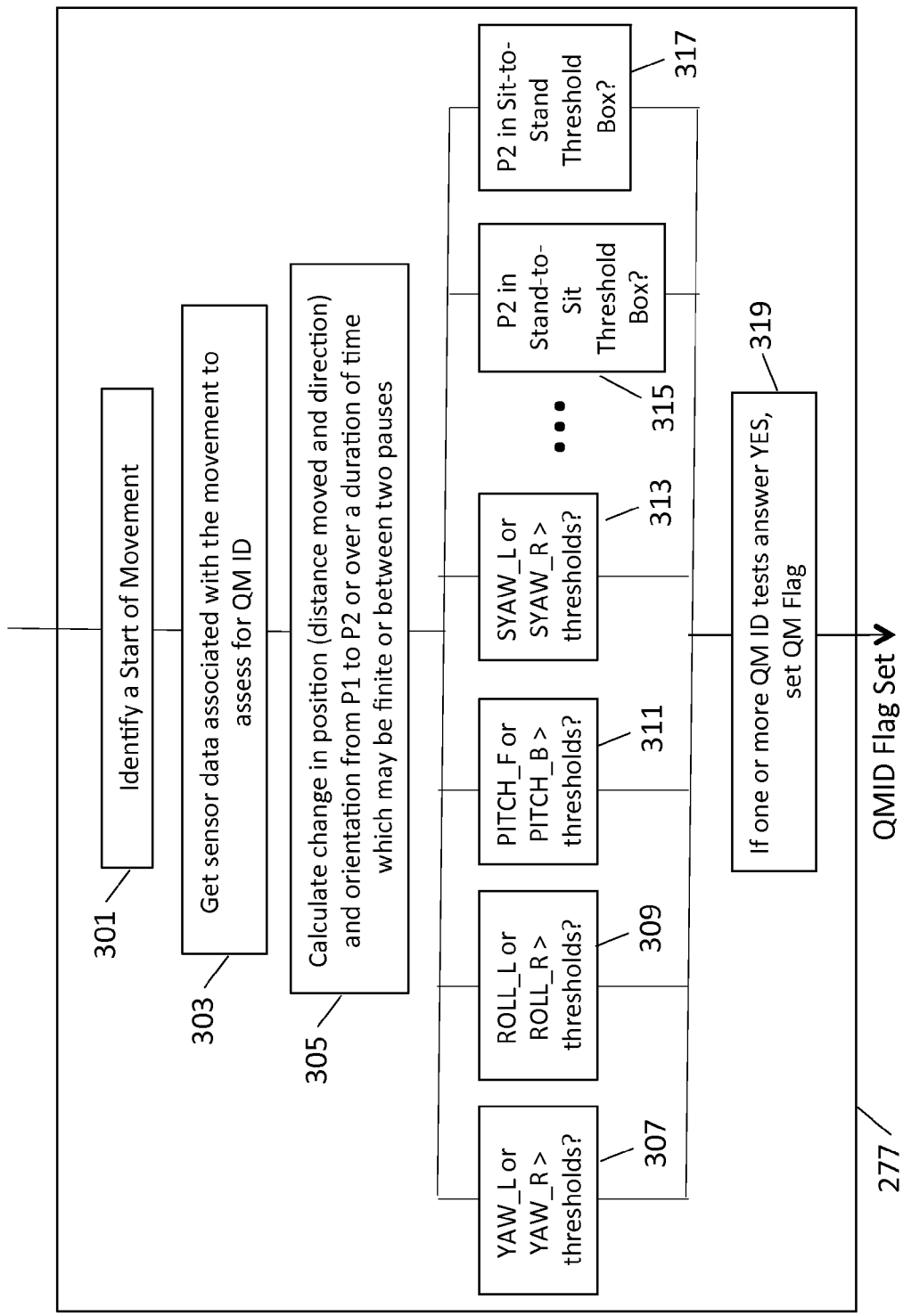
FIG. 20 illustrates a block diagram of an embodiment of the signal processing flow for QMID.

The Qualifying Movement Identifier (QMID) block 277 is expanded in FIG. 20 to more clearly describe the processing steps performed to practice the QMID (or QM ID) presented in this disclosure. In this example, Rotation Thresholding and Position Thresholding are utilized. In an embodiment, the QMID processing steps can include identifying a movement of valid duration between two valid Pauses 301. The system can then retrieve the sensor data associated with the Movement stored in memory to calculate the change in user position during the movement between P1 and P2 305. The movement data can include the distance and direction and the change in orientation from P1 to P2. This data, along with the user's state at P1 may be used as inputs to the QMID test modules 307-317.

As discussed above, the system can determine if user movements are qualifying movements based upon the wearable device movement sensors. The calculated change in position and orientation data can be processed by one or more QMID test modules which can test the user movement data based upon threshold values or threshold boxes as described above. For example, the test modules can include a yaw rotation test module 307 which can identify a QM if the user movement exceeds YAW_L or YAW_R thresholds. Similarly, a roll test module 309 which can identify a QM if the user movement exceeds ROLL_L or ROLL_R thresholds can process the user movement data. A pitch test module 311 can identify a QM if the user movement exceeds PITCH_F or PITCH_B thresholds can also process the user movement data. As discussed, there can be different yaw thresholds for user standing yaw and user sitting yaw. These different thresholds depending on the user state, for example whether standing or sitting may be referred to as context dependent thresholds. A sitting yaw test module 313 can identify a QM if the user movement exceeds SYAW_L or SYAW_R thresholds.

As also discussed, QMs can be identified based upon movements into threshold boxes. The user movement data can be processed by a stand-to-sit threshold box test module 315. If the user movement is from P1 outside the stand-to-sit threshold box to P2 inside the stand-to-sit threshold box, the user movement can be a QM. Conversely, a sit-to-stand test module 317 can identify a QM if the user movement is from P1 outside the Sit-to-Stand threshold box to P2 inside the Sit-to-Stand threshold box. Various other test modules can be provided by the inventive system to test user movements. The test modules can include any threshold values for user movements based upon rotations, movements up and down, and movements down and up. Thus, some of the QMID test modules are not shown in FIG. 20. If one or more QMID tests are positive, set the QMID flag 319 and proceed to the next steps as shown in FIG. 19. If none of the QMID tests are positive, then the system can return to monitoring the sensor outputs resulting from user movements.

Figures 21A, 21B, 21C, 21D:
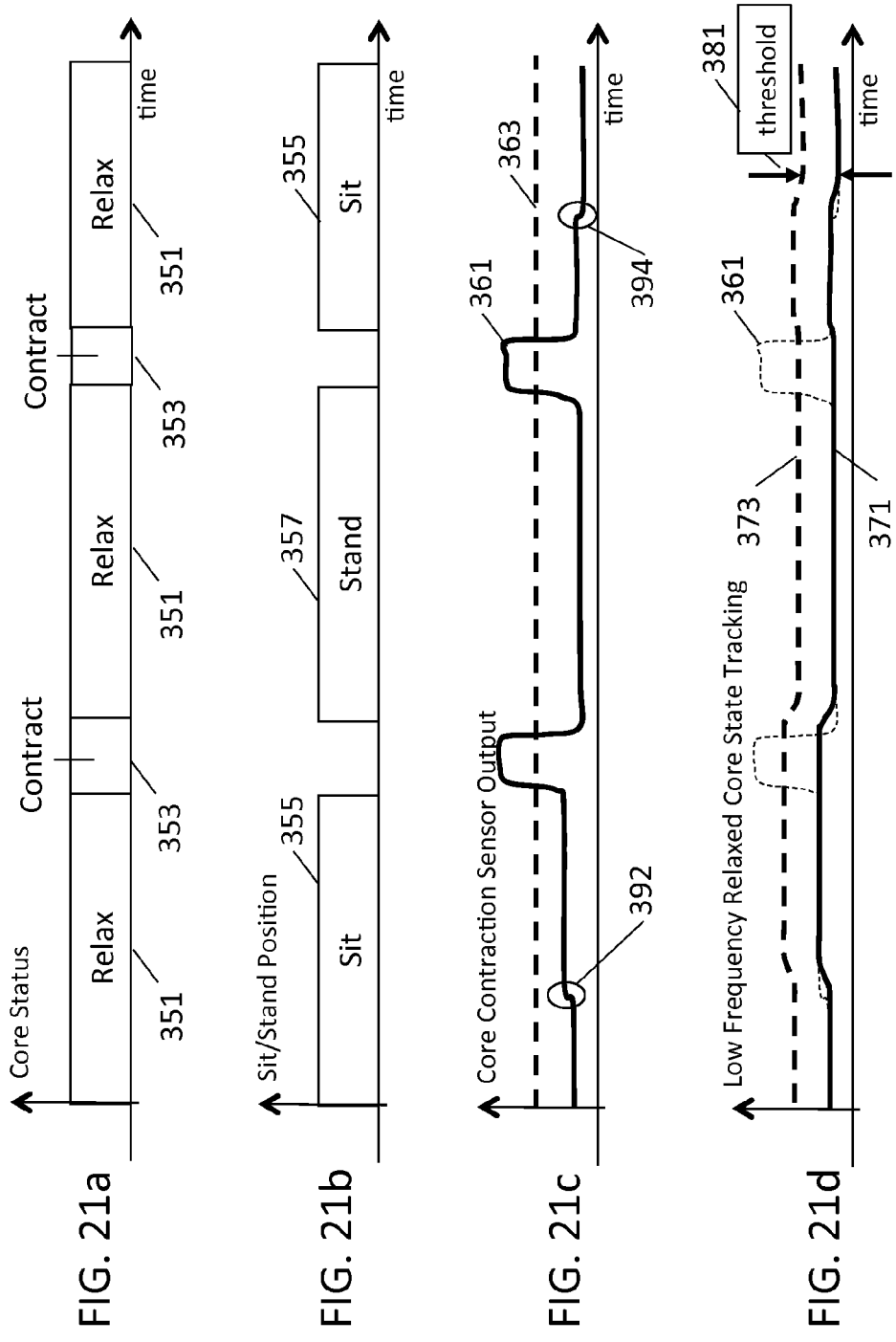
FIG. 21a illustrates a graph of a user's core status over time.
FIG. 21b illustrates a graph of a user position status over time.
FIG. 21c illustrates a graph of a core contraction sensor output over time.
FIG. 21d illustrates a graph of the core contraction sensor output tracked by a low frequency tracking block over time.

Different approaches may be used in the core status algorithm to process the signal from the core contraction sensor to identify a core contraction. An example to illustrate core contraction sensor signal processing is shown in FIGS. 21*a*-21*d*. FIG. 21*a* illustrates an example of a user's core status over time, including the core cycling between states of relax 351 and contract 353 during a stand-to-sit and sit-to-stand movement sequence. The user's corresponding positions of sit 355 and stand 357 over time are shown in FIG. 21*b*. FIG. 21*c* illustrates an example of a corresponding output signal 361 from the core contraction sensor. The core contraction sensor can be biased such that a low value signal can indicate a lower applied pressure to the core contraction sensor, corresponds to a relaxed core. A high value output signal from the core contraction sensor can indicate a higher applied pressure to the core contraction sensor, corresponding to a contracted core. In the illustrated graph there are two small steps 392, 394 shown in the core contraction sensor output signal 361. These small steps 392, 394 correspond to small movements of the user while sitting which results in movement of the wearable device on the elastic belt against the user's core muscles. These movements result in changes in applied pressure to the core contraction sensor, and result in changes in the core contraction sensor output 361 shown as the small steps 392, 394.

In an embodiment, a fixed threshold 363 is used to determine whether the core is contracted or relaxed. If the core contraction sensor output 361 is greater than the threshold 363, the core is determined to be contracted. If the core contraction sensor output 361 is less than the threshold 363, the core is determined to be relaxed. A limitation of this embodiment is that changes in the core contraction sensor output 361 due to movements of the user may reduce the amount the core contraction sensor output 361 needs to increase in order to identify or determine a core contraction, making the system susceptible to noise and user movements that may be incorrectly interpreted as a contracted core when the core is relaxed. The small steps 392, 394 are well below the fixed threshold 363 and are not determined by the system to be core contractions.

In another embodiment, core contraction sensor output 361 is tracked by a low-frequency tracking block with output 371 shown in FIG. 21*d*. This block tracks the core contraction sensor output 361 when a relaxed condition is determined. The tracking signal 371 can have a fixed threshold 381 that is added to the tracking signal 371 to define a variable threshold 373 which tracks the core contraction sensor output 371 when the core is determined to be in the relaxed state. In this configuration, a core contraction 361 may need to produce substantially higher output signal over the relaxed state core contraction sensor output 371 in order to exceed the variable threshold 373. Because the variable threshold 373 tracks the relaxed core output 371, the resulting threshold 373 may be more robust and less sensitive to noise and user movements that may be incorrectly identified as a contracted core when the core is relaxed.

Other approaches may be taken to implement the core status algorithm. In other embodiments, data from the other sensors may be combined with the core contraction sensor output 361 to improve the accuracy of identifying a core contraction. The core status as determined by the core status algorithm may be stored in memory with sensor data, combined sensor data, and calculated values and used to determine whether a QM is protected or unprotected.

Embodiments disclosed may enable a simple and easy to understand approach to teach users to support their QMs with contraction of their core muscles. The teaching approach may be supplemented with illustrations of the inner core muscles, the spine, and the nerves from the spine to the lower extremities to emphasize the role of the core for stabilizing the lumbosacral junction. The illustrations may two-dimensional or three-dimensional images. Animations or videos may also be utilized by a user to develop a mental image of the role of core support. The presented strategy to teach a user to use deliberate movements that are basic and separated by pauses may enable and encourage the user to maintain balance and provide the user time to think to contract their core prior to, hold their core contracted through, and to relax their core following QMs.

Embodiments disclosed provide a comprehensive approach to identifying Qualifying Movements in basic every day movements utilizing, in part, inertial navigation methods. The inventive approaches described in this disclosure may be the first comprehensive approach to defining and developing algorithms operating on the outputs of low cost sensors in as few as one wearable device to identify Qualifying Movements. Embodiments utilizing these inventive concepts may be utilized in a device as part of a system to develop procedural memory in a user for support of their core during QMs.

The combination of the teaching paradigm and the comprehensive approach for using sensors to identify QMs result in a system that may be effective for supporting the development of procedural memory for core support during QMs. The algorithm aspect may be utilized apart from any specific teaching method and may be generally applied to address QM Identification. The teaching method may also be utilized with a device or system to develop procedural memory for support of the core during QMs, apart from any specific algorithm approach for QM Identification.

The figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing core contraction procedural memory, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A method for development of procedural memory for a core based support, comprising:
   providing a movement sensor and a core muscle contraction sensor in communication with a processor;
   detecting movements of a user who is standing or sitting with the movement sensor;
   transmitting movement signals from the movement sensor to the processor;
   detecting core muscle contractions of the user with the core muscle contraction sensor;
   transmitting core contraction signals from the core muscle contraction sensor to the processor;
   processing the movement signals with a qualifying movement algorithm running on the processor to determine that the movements of the user who is standing or sitting detected by the movement sensor are either qualifying movements that benefits from the core muscle contractions or non-qualifying movements that do not benefit from the core muscle contractions;
   detecting by the processor, a timing relationship between the qualifying movements and the core muscle contractions; and
   analyzing the timing relationship by the processor to determine that the qualifying movement is either a protected qualifying movement where the core muscle contractions of the user who is standing or sitting are detected by the core muscle contraction sensor during the qualifying movement detected by the movement sensor or an unprotected qualifying movement where the core muscle contraction is not detected by the core muscle contraction sensor during the qualifying movement detected by the movement sensor.

2. The method of claim 1 wherein the processing of the movement signals by the qualifying movement algorithm includes detecting non-movements of the user who is standing or sitting prior to a start of the movements.

3. The method of claim 1 wherein the processing of the movement signals by the qualifying movement algorithm includes detecting non-movements after an end of the movements.

4. The method of claim 1 wherein the processing of the movement signals by the qualifying movement algorithm includes detecting movements of the user who is standing or sitting for a duration of time.

5. The method of claim 4 further comprising:
   determining the duration of time that is optimized for a user; and
   storing the duration of time that is optimized for the user.

6. The method of claim 4 further comprising:
   determining the duration of time that is optimized for the qualifying movement; and
   storing the duration of time that is optimized for the qualifying movement.

7. The method of claim 1 wherein the processing of the movement signals by the qualifying movement algorithm includes calculating changes in position and orientation of the user from a start of the movements to an end of the movements.

8. The method of claim 1 wherein the processing of the movement signals with the qualifying movement algorithm includes determining that the movements of the user who is standing or sitting detected by the movement sensor are more likely to be a first of the qualifying movements than any of the non-qualifying movements.

9. The method of claim 1 wherein the processing of the movement signals with the qualifying movement algorithm includes determining that the movements of the user who is standing or sitting detected by the movement sensor are more likely to be a first of the qualifying movements than a second of the qualifying movements.

10. The method of claim 1 wherein the processing of the movement signals with the qualifying movement algorithm includes determining that the movements of the user who is standing or sitting detected by the movement sensor are more likely to be one of the non-qualifying movements than one of the qualifying movements.

11. The method of claim 1 wherein the movement sensor detects the movements of the user in X, Y and Z directions and the processing the movement signals with a qualifying movement algorithm includes determining that the movements of the user who is standing or sitting exceed a movement threshold value.

12. The method of claim 1 wherein the movement sensor detects the movements of the user in a three dimensional volume and the processing the movement signals with a qualifying movement algorithm includes determining that the movements of the user who is standing or sitting extend outside the three dimensional volume.

13. The method of claim 1 wherein the movement sensor detects the movements of the user in X, Y and Z directions and the processing the movement signals with a qualifying movement algorithm includes determining that the movements of the user who is standing or sitting exceed an X movement threshold value, a Y movement threshold value or a Z movement threshold value.

14. The method of claim 1 wherein the movement sensor detects the movements of the user in X, Y and Z directions and rotations of the user about X, Y and Z axes and the processing the movement signals with a qualifying movement algorithm includes determining that the movements or the rotations of the user who is standing or sitting exceed a movement threshold value and a rotation threshold value.

15. The method of claim 1 wherein the movement sensor detects the movements of the user in X, Y and Z directions and rotations of the user about X, Y and Z axes and the processing the movement signals with a qualifying movement algorithm includes determining that the movements or the rotations of the user who is standing or sitting exceed an X movement threshold value, a Y movement threshold value, a Z movement threshold value, an X axis rotational threshold value, a Y axis rotational threshold value or a Z axis rotational threshold value.

16. The method of claim 1 wherein the movement sensor detects the movements of the user who is standing or sitting in X, Y and Z directions and the qualifying movement algorithm includes identifying a detected qualifying movement based upon the movements of the user in X, Y and Z directions.

17. The method of claim 1 wherein the movement sensor detects the movements of the user in X, Y and Z directions and rotations of the user about X, Y and Z axes and qualifying movement algorithm includes identifying a detected qualifying movement based upon the movements of the user who is standing or sitting in X, Y and Z directions and the rotations of the user about the X, Y and Z axes.

18. The method of claim 1 wherein the processing of the movement signals with the qualifying movement algorithm includes neglecting the effects of DC offsets.

19. The method of claim 1 further comprising:
providing an output mechanism in communication with the processor;
wherein the processor transmits an output signal to the output mechanism, the output signal recommending a pause and a core contraction prior to performing the movements of the user who is standing or sitting.

20. The method of claim 1 wherein the detecting of the user with the movement sensor is performed while the user is performing an athletic movement.

* * * * *